United States Patent
Belardinelli et al.

(10) Patent No.: US 8,188,099 B2
(45) Date of Patent: May 29, 2012

(54) METHOD OF DECREASING HEPATOTOXIC SIDE EFFECTS USING $A_{2B}$ ADENOSINE RECEPTOR ANTAGONISTS

(75) Inventors: Luiz Belardinelli, Palo Alto, CA (US); Dewan Zeng, Palo Alto, CA (US); Hongyan Zhong, Mountain View, CA (US)

(73) Assignee: Gilead Sciences, Inc., Foster City, CA (US)

( * ) Notice: Subject to any disclaimer, the term of this patent is extended or adjusted under 35 U.S.C. 154(b) by 51 days.

(21) Appl. No.: 12/853,510

(22) Filed: Aug. 10, 2010

(65) Prior Publication Data

US 2011/0184002 A1 Jul. 28, 2011

Related U.S. Application Data

(62) Division of application No. 11/687,236, filed on Mar. 16, 2007, now Pat. No. 7,795,268.

(60) Provisional application No. 60/783,575, filed on Mar. 17, 2006.

(51) Int. Cl.
*A61K 31/522* (2006.01)
(52) U.S. Cl. .................................... 514/263.2
(58) Field of Classification Search ............ None
See application file for complete search history.

(56) References Cited

U.S. PATENT DOCUMENTS

| 7,625,881 | B2 | 12/2009 | Kalla et al. |
| 7,795,268 | B2 | 9/2010 | Zeng et al. |
| 2003/0139428 | A1 | 7/2003 | Kalla et al. |
| 2004/0053982 | A1 | 3/2004 | Press et al. |
| 2004/0176399 | A1 | 9/2004 | Elzein et al. |
| 2005/0261248 | A1 | 11/2005 | Vidal Juan et al. |

FOREIGN PATENT DOCUMENTS

| WO | WO-0242298 A1 | 5/2002 |
| WO | WO-03101455 A2 | 12/2003 |
| WO | WO-2004086052 A2 | 10/2004 |
| WO | WO-2005070926 A1 | 8/2005 |

OTHER PUBLICATIONS

Chan et al., Drug Development Research, 56(4), (Aug. 2002), p. 557.
Kolachala et al., "TNF-alpha Upregulates Adenosine 2b (A2b) Receptor Expression and Signaling in Intestinal Epithelial Cells: a Basis for A2bR Overexpression in Colitis", Cellular and Molecular Life Sciences, vol. 62, No. 22, Nov. 2005, pp. 2647-2657.
Link, J.T., "Pharmacological Regulation of Hepatic Glucose Production", Current Opinion in Investigational Drugs, Pharmapress, U.S., vol. 4., No. 4, 2003, pp. 421-429.
Thuluvath et al., Digestive Diseases & Sciences, 48(3) (Mar. 2003), pp. 542-550.
Vippagunta et al., Advanced Drug Delivery Reviews, 48 (2001), pp. 3-26.
Zong et al., "Synergy Between A2B Adenosine Receptors and Hypoxia in Activating Human Lung Fibroblasts", American Journal of Respiratory Cell and Molecular Biology, American lung Association, New York, NY, U.S.. vol. 32, No. 1, Jan. 2005, pp. 2-8.
Belikov, V.G. (1993), "Phararmaceutical Chemistry", *High School*, pp. 43-47.

*Primary Examiner* — Phyllis G. Spivack
(74) *Attorney, Agent, or Firm* — Foley & Lardner LLP

(57) ABSTRACT

The invention is related to a method of decreasing hepatotoxic side effects using an A2B adenosine receptor antagonist and utility in the treatment of liver damage caused by undergoing hepatotoxic treatment, such as chemotherapy or radiation. The invention also relates to pharmaceutical compositions for use in the method.

6 Claims, 6 Drawing Sheets

A

B

METHOD OF DECREASING HEPATOTOXIC SIDE EFFECTS USING A$_{2B}$ ADENOSINE RECEPTOR ANTAGONISTS

This application is a divisional of U.S. patent application Ser. No. 11/687,236, filed Mar. 16, 2007, which claims priority to U.S. Provisional Patent Application Ser. No. 60/783,575, filed Mar. 17, 2006, the entirety of which are incorporated herein by reference.

FIELD OF THE INVENTION

The present invention relates to methods of preventing and treating hepatic disease using A$_{2B}$ adenosine receptor antagonists. This invention finds utility in the treatment and prevention of liver damage caused by alcohol abuse, surgical intervention, viral hepatitis, the ingestion of hepatotoxic drugs, or other hepatic diseases. The invention also relates to pharmaceutical compositions for use in the method.

BACKGROUND

Hepatic disease can take a wide variety of forms including, but not limited to, necrosis, steatosis, fibrosis, and cholestatis. Other forms of liver disease can result from the ingestion of hepatotoxic medicines such as chemotherapy and cancer drugs, antibiotics, analgesics, antiemetics, and other medications. Also, alcohol and drug abuse are well known causes of liver disease. Typical causes of hepatic disease include, but are not limited to, viral and alcoholic hepatitis, Wilson's disease, hemochromatosis, steatosis, and nonalcoholic steatohepatitis (NASH).

Hepatic fibrosis is a common aspect of many, if not all, hepatic diseases and is defined as the formation of scar tissue in the liver. The scarring develops as the liver attempts to repair cellular damage induced by the ingestion of hepatotoxins, as a consequence of chronic liver inflammation, or as a consequence of physical insult. Hepatic fibrosis may also result as a consequence of surgical intervention and hepatotoxic drug therapy, i.e., liver replacement or repair or chemotherapy. In many cases, hepatic fibrosis produces permanent scarring of the hepatic tissue, a condition commonly referred to as cirrhosis.

Recent studies have disclosed that adenosine plays a role in the development and progression of hepatic fibrosis. Chunn et al. (2006) *Am. J. Physiol Lung Cell Mol Physiol,* 290(3): L579-87, detected increased hepatic fibrosis in adenosine deaminase (ADA) deficient mice. The mice utilized by Chunn et al. are genetically engineered to possess partial ADA enzyme activity and thereby accumulate adenosine of a prolonged period of time.

Adenosine is a naturally occurring nucleoside, which exerts its biological effects by interacting with a family of adenosine receptors known as A$_1$, A$_{2A}$, A$_{2B}$, and A$_3$, all of which modulate important physiological processes. Of the various receptors, A$_{2B}$ adenosine receptors have been shown to modulate the synthesis and release of angiogenic factors and inflammatory cytokine and chemokines and are believed to be most significantly involved in inflammatory conditions via their connection to mast cell activation, vasodilation, and regulation of cell growth (See Adenosine A$_{2B}$ Receptors as Therapeutic Targets, *Drug Dev Res* 45:198; Feoktistov et al., *Trends Pharmacol Sci* 19:148-153).

Surprisingly, it has now been found that A$_{2B}$ adenosine receptor antagonists are also useful in the prevention and treatment of hepatic disease. Accordingly, it is desired to provide a method of treating and/or preventing hepatic disease by administration of compounds that are potent, fully or partially selective, A$_{2B}$ antagonists, i.e., compounds that inhibit the A$_{2B}$ adenosine receptor.

SUMMARY OF THE INVENTION

In one embodiment of the invention, a method is provided for the treatment and prevention of hepatic disease by administration of a therapeutically effective amount of an A$_{2B}$ adenosine receptor antagonist to a mammal in need thereof. The hepatic disease may take the form of necrosis, fibrosis, cholestatis, cirrhosis, viral and alcoholic hepatitis, Wilson's disease, hemochromatosis, steatosis, and nonalcoholic steatohepatitis (NASH) or the hepatic disease may be the consequence of surgical intervention or drug therapy with a hepatotoxic agent, i.e., liver replacement or repair or chemotherapy.

In a second embodiment of the invention, a method is provided for decreasing the hepatotoxic side effects of chemotherapy or radiation by administration of a therapeutically effective amount of an A$_{2B}$ adenosine receptor antagonist to a mammal undergoing such treatment.

In another embodiment of the invention, a method is provided for the treatment and prevention of hepatic disease by administration to a mammal in need thereof, a therapeutically effective amount of an A$_{2B}$ adenosine receptor antagonist having the structure of Formula I or Formula II:

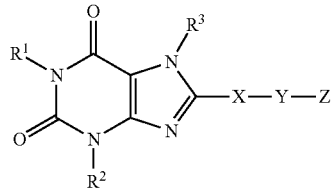

Formula I

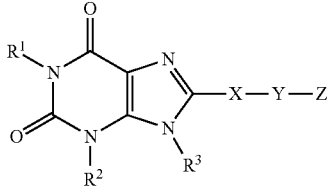

Formula II wherein:

R$^1$ and R$^2$ are independently chosen from hydrogen, optionally substituted alkyl, or a group -D-E, in which D is a covalent bond or alkylene, and E is optionally substituted alkoxy, optionally substituted cycloalkyl, optionally substituted aryl, optionally substituted heteroaryl, optionally substituted heterocyclyl, optionally substituted alkenyl or optionally substituted alkynyl, with the proviso that when D is a covalent bond E cannot be alkoxy;

R$^3$ is hydrogen, optionally substituted alkyl or optionally substituted cycloalkyl;

X is optionally substituted arylene or optionally substituted heteroarylene;

Y is a covalent bond or alkylene in which one carbon atom can be optionally replaced by —O—, —S—, or —NH—, and is optionally substituted by hydroxy, alkoxy, optionally substituted amino, or —COR, in which R is hydroxy, alkoxy or amino; and Z is optionally substituted monocyclic aryl or optionally substituted monocyclic heteroaryl; or Z is hydrogen when X is optionally substituted heteroarylene and Y is a covalent bond.

In yet another embodiment of the invention, pharmaceutical formulations are provided, comprising a therapeutically effective amount of an $A_{2B}$ adenosine receptor antagonist, and at least one pharmaceutically acceptable carrier. The formulation is preferably for oral administration.

One preferred group of compounds of Formula I and II are those in which $R^1$ and $R^2$ are independently hydrogen, optionally substituted lower alkyl, or a group -D-E, in which D is a covalent bond or alkylene, and E is optionally substituted phenyl, optionally substituted cycloalkyl, optionally substituted alkenyl, or optionally substituted alkynyl, particularly those in which $R^3$ is hydrogen.

Within this group, a first preferred class of compounds include those in which $R^1$ and $R^2$ are independently lower alkyl optionally substituted by cycloalkyl, preferably n-propyl, and X is optionally substituted phenylene. Within this class, a preferred subclass of compounds are those in which Y is alkylene, including alkylene in which a carbon atom is replaced by oxygen, preferably —O—CH$_2$—, more especially where the oxygen is the point of attachment to phenylene. Within this subclass, it is preferred that Z is optionally substituted oxadiazole, particularly optionally substituted [1,2,4]-oxadiazol-3-yl, especially [1,2,4]-oxadiazol-3-yl substituted by optionally substituted phenyl or optionally substituted pyridyl.

A second preferred class of compounds include those in which X is optionally substituted 1,4-pyrazolene. Within this class, a preferred subclass of compounds are those in which Y is a covalent bond or alkylene, especially lower alkylene, and Z is hydrogen, optionally substituted phenyl, optionally substituted pyridyl, or optionally substituted oxadiazole. Within this subclass, one preferred embodiment includes compounds in which $R^1$ is lower alkyl optionally substituted by cycloalkyl, and $R^2$ is hydrogen. A more preferred embodiment includes those compounds in which Y is —(CH$_2$)— or —CH(CH$_3$)— and Z is optionally substituted phenyl, or Y is —(CH$_2$)— or —CH(CH$_3$)— and Z is optionally substituted oxadiazole, particularly 3,5-[1,2,4]-oxadiazole, or Y is —(CH$_2$)— or —CH(CH$_3$)— and Z is optionally substituted pyridyl. Within this subclass, also preferred are those compounds in which $R^1$ and $R^2$ are independently lower alkyl optionally substituted by cycloalkyl, especially n-propyl. More preferred are those compounds in which Y is a covalent bond, —(CH$_2$)— or —CH(CH$_3$)— and Z is hydrogen, optionally substituted phenyl, or optionally substituted pyridyl, particularly where Y is a covalent bond and Z is hydrogen.

An additional subgroup of preferred compounds are those in which $R^3$ is a substituted alkyl group of the formula —CHR$^4$OR$^5$ so that the compounds have the structure of Formula III:

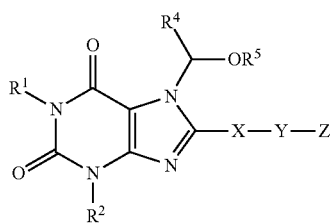

wherein:
$R^4$ is hydrogen or methyl; and
$R^5$ is —C(O)R, in which R is independently optionally substituted lower alkyl, optionally substituted aryl, or optionally substituted heteroaryl; or $R^5$ is —P(O)(OR$^6$)$_2$, in which R$^6$ is hydrogen or lower alkyl optionally substituted by phenyl or heteroaryl;
and the pharmaceutically acceptable salts thereof.

At present, the preferred compounds for use in the invention include, but are not limited to:
1-propyl-8-(1-{[3-(trifluoromethyl)phenyl]-methyl}pyrazol-4-yl)-1,3,7-trihydropurine-2,6-dione;
1-propyl-8-[1-benzylpyrazol-4-yl]-1,3,7-trihydropurine-2,6-dione;
1-butyl-8-(1-{[3-fluorophenyl]methyl}pyrazol-4-yl)-1,3,7-trihydropurine-2,6-dione;
1-propyl-8-[1-(phenylethyl)pyrazol-4-yl]-1,3,7-trihydropurine-2,6-dione;
8-(1-{[5-(4-chlorophenyl)(1,2,4-oxadiazol-3-yl)]methyl}pyrazol-4-yl)-1-propyl-1,3,7-trihydropurine-2,6-dione;
8-(1-{[5-(4-chlorophenyl)(1,2,4-oxadiazol-3-yl)]methyl}pyrazol-4-yl)-1-butyl-1,3,7-trihydropurine-2,6-dione;
1,3-dipropyl-8-pyrazol-4-yl-1,3,7-trihydropurine-2,6-dione;
1-methyl-3-sec-butyl-8-pyrazol-4-yl-1,3,7-trihydropurine-2,6-dione;
1-cyclopropylmethyl-3-methyl-8-{1-[(3-trifluoromethylphenyl)methyl]pyrazol-4-yl}-1,3,7-trihydropurine-2,6-dione;
1,3-dimethyl-8-{1-[(3-fluorophenyl)methyl]pyrazol-4-yl}-1,3,7-trihydropurine-2,6-dione;
3-methyl-1-propyl-8-{1-[(3-trifluoromethylphenyl)methyl]pyrazol-4-yl}-1,3,7-trihydropurine-2,6-dione;
3-ethyl-1-propyl-8-{1-[(3-trifluoromethylphenyl)methyl]pyrazol-4-yl}-1,3,7-trihydropurine-2,6-dione;
1,3-dipropyl-8-(1-{[3-(trifluoromethyl)phenyl]methyl}pyrazol-4-yl)-1,3,7-trihydropurine-2,6-dione;
1,3-dipropyl-8-{1-[(3-fluorophenyl)methyl]pyrazol-4-yl}-1,3,7-trihydropurine-2,6-dione;
1-ethyl-3-methyl-8-{1-[(3-fluorophenyl)methyl]pyrazol-4-yl}-1,3,7-trihydropurine-2,6-dione;
1,3-dipropyl-8-{1-[(2-methoxyphenyl)methyl]pyrazol-4-yl}-1,3,7-trihydropurine-2,6-dione;
1,3-dipropyl-8-(1-{[3-(trifluoromethyl)-phenyl]ethyl}pyrazol-4-yl)-1,3,7-trihydropurine-2,6-dione;
1,3-dipropyl-8-{1-[(4-carboxyphenyl)methyl]pyrazol-4-yl}-1,3,7-trihydropurine-2,6-dione;
2-[4-(2,6-dioxo-1,3-dipropyl(1,3,7-trihydropurin-8-yl))pyrazolyl]-2-phenylacetic acid;
8-{4-[5-(2-methoxyphenyl)-[1,2,4]oxadiazol-3-ylmethoxy]phenyl}-1,3-dipropyl-1,3,7-trihydropurine-2,6-dione;
8-{4-[5-(3-methoxyphenyl)-[1,2,4]oxadiazol-3-ylmethoxy]phenyl}-1,3-dipropyl-1,3,7-trihydropurine-2,6-dione;
8-{4-[5-(4-fluorophenyl)-[1,2,4]oxadiazol-3 ethoxy]phenyl}-1,3-dipropyl-1,3,7-trihydropurine-2,6-dione.
1-(cyclopropylmethyl)-8-[1-(2-pyridylmethyl)pyrazol-4-yl]-1,3,7-trihydropurine-2,6-dione;
1-n-butyl-8-[1-(6-trifluoromethylpyridin-3-ylmethyl)pyrazol-4-yl]-1,3,7-trihydropurine-2,6-dione;
8-(1-{[3-(4-chlorophenyl)(1,2,4-oxadiazol-5-yl)]methyl}pyrazol-4-yl)-1,3-dipropyl-1,3,7-trihydropurine-2,6-dione;
1,3-dipropyl-8-[1-({5-[4-(trifluoromethyl)phenyl] isoxazol-3-yl}methyl)pyrazol-4-yl]-1,3,7-trihydropurine-2,6-dione;
1,3-dipropyl-8-[1-(2-pyridylmethyl)pyrazol-4-yl]-1,3,7-trihydropurine-2,6-dione;
3-{[4-(2,6-dioxo-1,3-dipropyl-1,3,7-trihydropurin-8-yl)pyrazolyl]methyl}benzoic acid;
1,3-dipropyl-8-(1-{[6-(trifluoromethyl)(3-pyridyl)]methyl}pyrazol-4-yl)-1,3,7-trihydropurine-2,6-dione;

1,3-dipropyl-8-{1-[(3-(1H-1,2,3,4-tetraazol-5-yl)phenyl)
  methyl]pyrazol-4-yl}1,3,7-trihydropurine-2,6-dione;
6-{[4-(2,6-dioxo-1,3-dipropyl-1,3,7-trihydropurin-8-yl)
  pyrazolyl]methyl}pyridine-2-carboxylic acid;
3-ethyl-1-propyl-8-[1-(2-pyridylmethyl)pyrazol-4-yl]-1,3,
  7-trihydropurine-2,6-dione;
8-(1-{[5-(4-chlorophenyl)isoxazol-3-yl]methyl}pyrazol-4-
  yl)-3-ethyl-1-propyl-1,3,7-trihydropurine-2,6-dione;
8-(1-{[3-(4-chlorophenyl)(1,2,4-oxadiazol-5-yl)]
  methyl}pyrazol-4-yl)-3-ethyl-1-propyl-1,3,7-trihydropu-
  rine-2,6-dione;
3-ethyl-1-propyl-8-(1-{[6-(trifluoromethyl)(3-pyridyl)]
  methyl}pyrazol-4-yl)-1,3,7-trihydropurine-2,6-dione;
1-(cyclopropylmethyl)-3-ethyl-8-(1-{[6-(trifluoromethyl)
  (3-pyridyl)]methyl}pyrazol-4-yl)-1,3,7-trihydropurine-2,
  6-dione;
3-ethyl-1-(2-methylpropyl)-8-(1-{[6-(trifluoromethyl)(3-
  pyridyl)]methyl}pyrazol-4-yl)-1,3,7-trihydropurine-2,6-
  dione;
[3-ethyl-2,6-dioxo-1-propyl-8-(1-{[3-(trifluoromethyl)phe-
  nyl]methyl}pyrazol-4-yl)-1,3,7-trihydropurin-7-yl]me-
  thyl acetate;
[3-ethyl-2,6-dioxo-1-propyl-8-(1-{[3-(trifluoromethyl)phe-
  nyl]methyl}pyrazol-4-yl)-1,3,7-trihydropurin-7-yl]me-
  thyl 2,2-dimethylpropanoate;
[3-ethyl-2,6-dioxo-1-propyl-8-(1-{[3-(trifluoromethyl)phe-
  nyl]methyl}pyrazol-4-yl)-1,3,7-trihydropurin-7-yl]me-
  thyl butanoate; and
[3-ethyl-2,6-dioxo-1-propyl-8-(1-{[3-(trifluoromethyl)phe-
  nyl]methyl}-pyrazol-4-yl)(1,3,7-trihydropurin-7-yl)]me-
  thyl dihydrogen phosphate.

DETAILED DESCRIPTION OF THE INVENTION

Definitions and General Parameters

Figure 1:
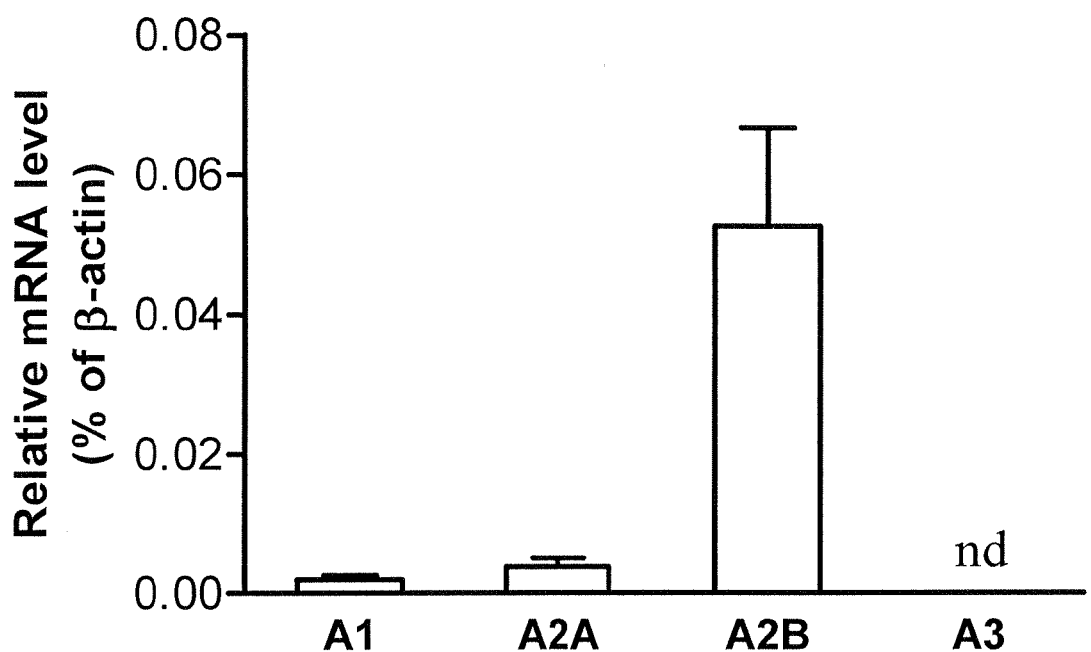
FIG. 1 graphically illustrates the mRNA levels of AdoR subtypes in HHSCs. Total RNA isolated from HHSCs was subjected to real-time RT-PCR analysis. The relative levels of the AdoR transcripts are presented as percentages of the β-actin transcript. Data shown are averages±SEM (n=4). nd denotes not detected.

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, aryloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or 2) an alkyl group as defined above that is interrupted by 1-10 atoms independently chosen from oxygen, sulfur and $NR_a$—, where $R_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or 3) an alkyl group as defined above that has both 1, 2, 3, 4 or 5 substituents as defined above and is also interrupted by 1-10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1-10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1, 2, 3, 4, 5, or 6 carbon atoms.

The term "lower alkylene" refers to a diradical of a branched or unbranched saturated hydrocarbon chain, preferably having from 1, 2, 3, 4, 5, or 6 carbon atoms.

The term "substituted alkylene" refers to:
(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
(2) an alkylene group as defined above that is interrupted by 1-20 atoms independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH═CH$_2$), 1-propylene or allyl (—CH$_2$CH═CH$_2$), isopropylene (—C(CH$_3$)═CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and S(O)$_n$R, where R$_1$ is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, $CF_3$, amino, substituted amino, cyano, or —$S(O)_nR$, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained by the definition for the aryl or arylene substituent, such aryl or arylene groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, $SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —$NH_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y—Z, in which Y is optionally substituted alkylene and Z is alkenyl, cycloalkenyl, or alkynyl, Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "carboxyalkyl" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, $CF_3$, amino, substituted amino, cyano, or —$S(O)_nR$, in which R is alkyl, aryl, or heteroaryl and n is 0, 1 or 2.

The term "cycloalkyl" refers to carbocyclic groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethylbicyclo[2.2.1]hept-2-yl, (2,3,3-trimethylbicyclo [2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-oxide and N-alkoxy derivatives of nitrogen containing heteroaryl compounds, for example pyridine-N-oxide derivatives.

The term "heteroarylene" refers to a diradical of a heteroaryl group as defined above. This term is exemplified by groups such as 2,5-imidazolene, 3,5-[1,2,4]oxadiazolene, 2,4-oxazolene, 1,4-pyrazolene, and the like. For example, 1,4-pyrazolene is:

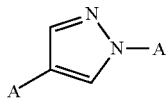

where A represents the point of attachment.

Unless otherwise constrained by the definition for the heteroaryl or heteroarylene substituent, such heteroaryl or heterarylene groups can be optionally substituted with 1 to substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —$S(O)_2R$, in which R is alkyl, aryl, or heteroaryl. "Substituted sulfone" refers to a group —$S(O)_2R$, in which R is substituted alkyl, substituted aryl, or substituted heteroaryl, as defined herein.

The term "keto" refers to a group —C(O)—.

The term "thiocarbonyl" refers to a group —C(S)—.

The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I and Formula II" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

"Topical administration" shall be defined as the delivery of the therapeutic agent to the surface of the wound and adjacent epithelium.

"Parenteral administration" is the systemic delivery of the therapeutic agent via injection to the patient.

The term "therapeutically effective amount" refers to that amount of a compound of Formula I that is sufficient to effect treatment, as defined below, when administered to a mammal in need of such treatment. The therapeutically effective amount will vary depending upon the specific activity of the therapeutic agent being used, and the age, physical condition, existence of other disease states, and nutritional status of the patient. Additionally, other medication the patient may be receiving will effect the determination of the therapeutically effective amount of the therapeutic agent to administer.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amities, di(substituted alkenyl)amines, tri(substituted alkenyl) amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl)amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is n-propyl, $R^2$ and $R^3$ are hydrogen, X is pyrazol-4-ylene, Y is methylene, and Z is 5-(4-chlorophenyl) (1,2,4-oxadiazol-3-yl,

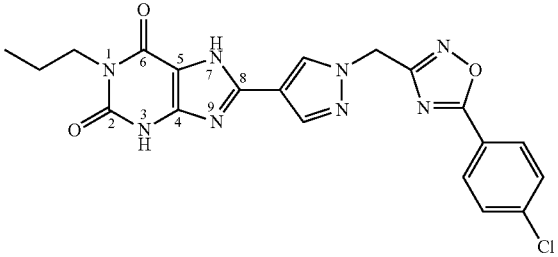

which is named:
8-(1-{[5-(4-chlorophenyl)(1,2,4-oxadiazol-3-yl)] methyl}pyrazol-4-yl)-1-propyl-1,3,7-trihydropurine-2,6-dione.

The Method of the Invention

The present invention relates to methods of preventing and/or treating hepatic disease by administration of a therapeutically effective amount of a $A_{2B}$ adenosine receptor antagonist to a mammal in need thereof. While not wishing to be bound by theory, it is believed that the ability $A_{2B}$ adenosine receptor antagonist to prevent fibrogenesis provides these compounds with the ability to prevent and treat hepatic disease.

As hepatic fibrogenesis is a significant component of viral and alcoholic hepatitis, Wilson's disease, hemochromatosis, steatosis, and nonalcoholic steatohepatitis, and may be the result of a surgical insult, i.e, liver replacement or repair, or hepatotoxic medical treatment, i.e., radiation, chemotherapy drugs, antibiotics, antiemetics, and the like, the method of the invention will generally involve administration of an $A_{2B}$ adenosine receptor antagonist to a patient suffering from one of the aforementioned conditions or undergoing hepatotoxic treatment.

Chemotherapy and radiation therapy in the treatment of cancer are two of the most common types of hepatotoxic treatment. Hepatotoxic drugs used to treat cancer include, but are not limited to, adriamycin, methotrexate, 6 mercaptopurine, carboplatin, DTIC (dacarbazine), BiCNU, L-asparaginase, and pentostatin.

Other drugs known to have hepatotoxic side effects include, but are not limited to, acebutolol; acetaminophen; actinomycin d; adrenocortical steroids; adriamycin; allopurinol; amoxicillin/clavulanate; anabolic steroids; anti-inflammatory drugs; antithyroid drugs; aspirin; atenolol; azathioprine; captopril; carbamazepine; carbimazole; carmustine; cephalosporins; chlordiazepoxide; chlorpromazine; chlorpromazine/valproic acid; chlorpropamide; chlorpropamide/erythromycin (combination); cimetidine; cloxacillin flecainide; cyclophosphamide; cyclophosphamide/cyclosporine; cyclosporine; dacarbazine; danazol; dantrolene; diazepam; diclofenac; diltiazem; disopyramide; enalapril; enflurane; erythromycin; ethambutol; ethionamide; flurazepam; flutamide; glyburide; gold; griseofulvin; haloperidol; halothane; hydralazine; ibuprofen; imipramine; indomethacin; isoniazid; ketoconazole; labetalol; maprotiline; mercaptopurine; methotrexate; methyldopa; methyltestosterone; metoprolol; mianserin; mitomycin; naproxen; nicotinic acid; nifedipine; nitrofurantoin; nonsteroidal; norethandrolone; oral contraceptives; oxacillin; para-aminosalicylic acid; penicillamine; penicillin; penicillins; phenelzine; phenindione; phenobarbital; phenothiazines; phenylbutazone; phenyloin; phenyloin troleandomycin; piroxicam; probenecid; procainamide; propoxyphene; pyrazinamide; quinidine; quinine; ranitidine; salicylates; sulfonamides; sulindac; tamoxifen; terbinafine HCl (Lamisil, Sporanox); testosterone; tetracyclines; thiabendazole; thioquanine; thorotrast; tolbutamide; tricyclic antidepressants; valproic acid; verapamil; vincristine; and vitamin A.

The onset of hepatic fibrogenesis begins with activation of human hepatic stellate cells (HHSC). Upon activation, HHSCs begin to synthesize a fibrotic matrix that is rich in type 1 collagen. This fibrotic matrix ultimately results in the scarring traditionally referred to as hepatic fibrosis. Applicants have surprisingly discovered that the $A_{2B}$ adenosine receptor is involved in the development of hepatic fibrosis as activation of the $A_{2B}$ receptor in HHSCs induces the release of IL-6 and expression of a-smooth muscle actin, a marker for HHSC activation. The release of IL-6 has in turn been shown to stimulate collagen production. It has been discovered that inhibition of the $A_{2B}$ receptor reduces the NECA-induced IL-6 release and collagen production.

The $A_{2B}$ adenosine receptor antagonist is administered systemically as either an oral or IV formulation but may also be administered directly to the hepatic tissue via injection. This administration can be as a single dose or as repeated doses given at multiple designated intervals. It will readily be appreciated by those skilled in the art that the preferred dosage regimen will vary with the patient and severity of the condition being treated.

Pharmaceutical Compositions

When selected as the adenosine $A_{2B}$ receptor antagonist, the compounds of Formula I are usually administered in the form of pharmaceutical compositions. This invention therefore provides pharmaceutical compositions that contain, as the active ingredient, one or more of the compounds of Formula I or Formula II, or a pharmaceutically acceptable salt or ester thereof, and one or more pharmaceutically acceptable excipients, carriers, including inert solid diluents and fillers, diluents, including sterile aqueous solution and various organic solvents, solubilizers and adjuvants. The compounds of Formula I and/or Formula II may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

The $A_{2B}$ Adenosine Receptor Antagonists

Any $A_{2B}$ adenosine receptor antagonist may be used in the method of the invention. Numerous compounds that antagonize the $A_{2B}$ receptor are known in the art, as are methods for determining if a specific compound has such activity. For example, a review article by Feoktistov and Baggioni, ((1997) *Pharmacological Reviews* 49:381-402) reports the binding affinity of eight adenosine receptor agonists and eight antagonists for all four subtypes of adenosine receptors. References cited therein provide detailed descriptions of the procedures used. (Robeva et al, (1996) *J. Drug Dev. Res* 39:243-252; Jacobson et al (1996) *Drug Dev. Res.* 39:289-300; Feoktistov and Baggioni (1993) *Molecular Pharmacology* 43:909-914). Effective methods for determining the binding affinity of a compound for a receptor use a radiolabeled agonist or antagonist and correlation of the binding of that compound to a membrane fraction known to contain that receptor; for example, to determine whether a compound is an $A_{2B}$ antagonist, the membrane fraction would contain the $A_{2B}$ adenosine receptor. Another particularly effective procedure for determining whether a compound is an $A_{2B}$ antagonist is reported in U.S. Pat. No. 5,854,081.

Compounds selective for the $A_{2B}$ receptor subtype are therefore preferred for the present methods. An example, but not a limitation, of such a compound is 3-n-propylxanthine (enprofylline). Suitable compounds are also disclosed in U.S. Pat. No. 6,545,002. Compounds that antagonize other receptors in addition to the $A_{2B}$ receptor are also suitable for use in the present invention. One example of such a compound is 1,3-dipropyl-8-(p-acrylic)phenylxanthine.

One particularly preferred class of $A_{2B}$ adenosine receptor antagonists are those disclosed in copending and commonly assigned U.S. Pat. No. 6,825,349, in copending and commonly assigned U.S. patent application Ser. No. 10/719,102, which published as U.S. Patent Application Publication No. 20040176399, and in copending and commonly assigned U.S. patent application Ser. No. 11/453,414, which published as U.S. Patent Application Publication No. 20060293283. The compounds disclosed in these applications have the structure of Formula I, II, and III as presented in the Summary of the Invention above and can be synthesized as described in the references or as detailed below.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula I and II

One preferred method of preparing compounds of Formula I or II where $R^3$ is hydrogen is shown in Reaction Scheme I.

REACTION SCHEME I

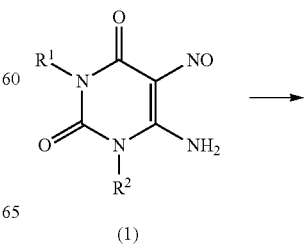

(1)

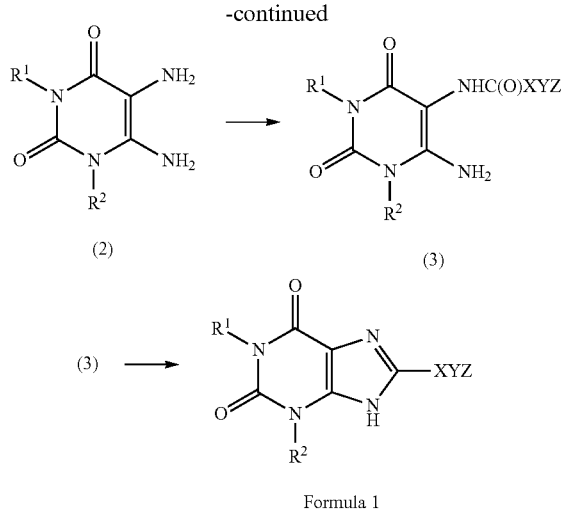

(2)  (3)

Formula 1

Step 1—Preparation of Formula (2)

The compound of formula (2) is made from the compound of formula (1) by a reduction step. Conventional reducing techniques may be used, for example using sodium dithionite in aqueous ammonia solution; preferably, reduction is carried out with hydrogen and a metal catalyst. The reaction is carried out at in an inert solvent, for example methanol, in the presence of a catalyst, for example 10% palladium on carbon catalyst, under an atmosphere of hydrogen, preferably under pressure, for example at about 30 psi, for about 2 hours. When the reaction is substantially complete, the product of formula (2) is isolated by conventional means to provide a compound of formula (2).

Step 2—Preparation of Formula (3)

The compound of formula (2) is then reacted with a carboxylic acid of the formula Z—Y—X—CO$_2$H in the presence of a carbodiimide, for example 1-(3-dimethylaminopropyl)-3-ethylcarbodiimide hydrochloride. The reaction is conducted in a protic solvent, for example methanol, ethanol, propanol, and the like, preferably methanol, at a temperature of about 20-30° C., preferably about room temperature, for about 12-48 hours, preferably about 16 hours. When the reaction is substantially complete, the product of formula (3) is isolated conventionally, for example by removal of the solvent under reduced pressure, and washing the product. Alternatively, the next step can be carried out without any further purification.

Alternative Preparation of a Compound of Formula (3)

Alternatively, the carboxylic acid of the formula Z—Y—X—CO$_2$H is first converted to an acid halide of the formula Z—Y—X—C(O)L, where L is chloro or bromo, by reacting with a halogenating agent, for example thionyl chloride or thionyl bromide, preferably thiony chloride. Alternatively, oxalyl chloride, phosphorus pentachloride or phosphorus oxychloride may be used. The reaction is preferably conducted in the absence of a solvent, using excess halogenating agent, for example at a temperature of about 60-80° C., preferably about 70° C., for about 1-8 hours, preferably about 4 hours. When the reaction is substantially complete, the product of formula Z—Y—X—C(O)L is isolated conventionally, for example by removal of the excess halogenating agent under reduced pressure.

The product is then reacted with a compound of formula (2) in an inert solvent, for example acetonitrile, in the presence of a tertiary base, for example triethylamine. The reaction is conducted at an initial temperature of about 0 C, and then allowed to warm to 20-30° C., preferably about room temperature, for about 12-48 hours, preferably about 16 hours. When the reaction is substantially complete, the product of formula (3) is isolated conventionally, for example by diluting the reaction mixture with water, filtering off the product, and washing the product with water followed by ether.

Step 3—Preparation of Formula I

The compound of formula (3) is then converted into a compound of Formula I by a cyclization reaction. The reaction is conducted in a protic solvent, for example methanol, ethanol, propanol, and the like, preferably methanol, in the presence of a base, for example potassium hydroxide, sodium hydroxide, sodium methoxide, sodium ethoxide, potassium t-butoxide, preferably aqueous sodium hydroxide, at a temperature of about 50-80° C., preferably about 80° C., for about 1-8 hours, preferably about 3 hours. When the reaction is substantially complete, the product of Formula I is isolated conventionally, for example by removal of the solvent under reduced pressure, acidifying the residue with an aqueous acid, filtering off the product, then washing and drying the product.

The compound of formula (1) may be prepared by various methods. One preferred method is shown in Reaction Scheme II.

REACTION SCHEME II

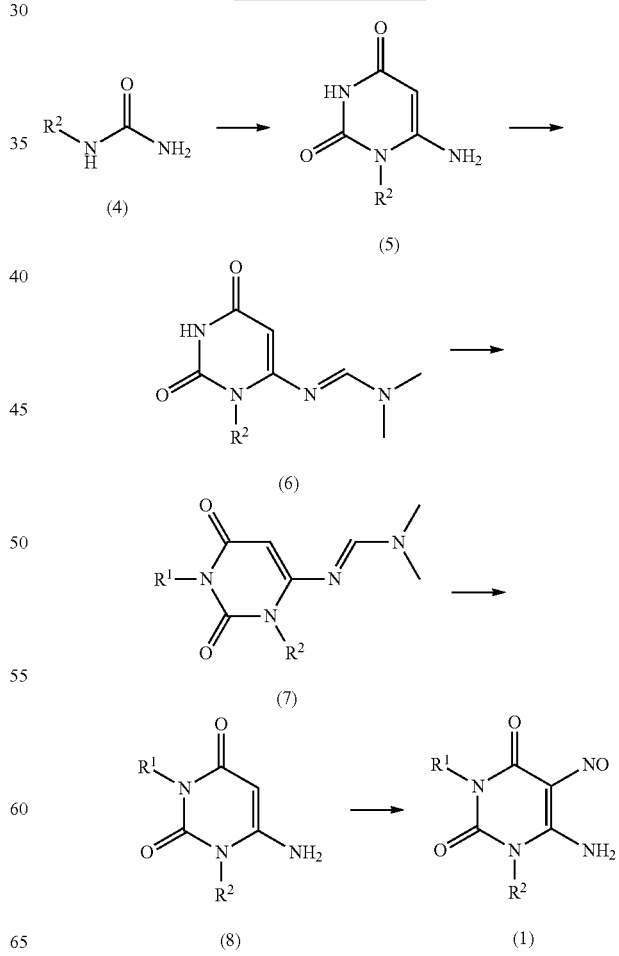

Step 1—Preparation of Formula (5)

The compound of formula (4) is either commercially available or prepared by means well known in the art. It is reacted with ethyl cyanoacetate in a protic solvent, for example ethanol, in the presence of a strong base, for example sodium ethoxide. The reaction is carried out at about reflux temperature, for about 4 to about 24 hours. When the reaction is substantially complete, the compound of formula (5) thus produced is isolated conventionally.

Step 2 and 3—Preparation of Formula (7)

The compound of formula (5) is reacted with the dimethylacetal of N,N-dimethylformamide in a polar solvent, for example N,N-dimethylformamide. The reaction is carried out at about 40° C., for about 1 hour. When the reaction is substantially complete, the compound of formula (6) thus produced is reacted with a compound of formula $R^1$Hal, where Hal is chloro, bromo, or iodo, in the presence of a base, for example potassium carbonate. The reaction is carried out at about 80° C., for about 4-24 hour. When the reaction is substantially complete, the product of formula (7) is isolated conventionally, for example by evaporation of the solvents under reduced pressure, and the residue is used in the next reaction with no further purification.

Step 4—Preparation of Formula (8)

The compound of formula (7) is reacted with aqueous ammonia in a polar solvent, for example suspended in methanol. The reaction is carried out at about room temperature, for about 1-3 days. When the reaction is substantially complete, the product of formula (8) is isolated conventionally, for example by chromatography over a silica gel column, eluting, for example, with a mixture of dichloromethane/methanol.

Step 5—Preparation of Formula (1)

The compound of formula (8) is then mixed with sodium nitrite in an aqueous acidic solvent, preferably acetic acid and water, for example 50% acetic acid/water. The reaction is carried out at a temperature of about 50-90° C., preferably about 70° C., for about 1 hour. When the reaction is substantially complete, the product of formula (1) is isolated by conventional means.

Alternatively, the reaction may be conducted in an aqueous solvent, for example dimethylformamide and water, and reacted with a strong acid, for example hydrochloric acid.

A compound of formula (8) can be prepared from a compound of formula (10) using a similar method, as shown in Reaction Scheme IIA.

REACTION SCHEME IIA

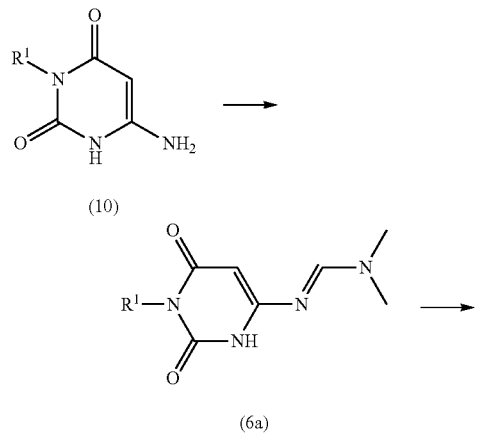

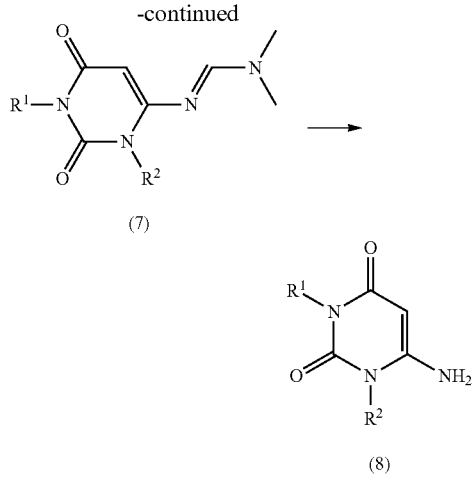

Step 2 and 3—Preparation of Formula (7)

The compound of formula (10) is reacted with the dimethylacetal of N,N-dimethylformamide in a polar solvent, for example N,N-dimethylformamide. The reaction is carried out at about 40° C., for about 1 hour. When the reaction is substantially complete, the compound of formula (6a) thus produced is reacted with a compound of formula $R^2$Hal, where Hal is chloro, bromo, or iodo, in the presence of a base, for example potassium carbonate. The reaction is carried out at about 80° C., for about 4-24 hour. When the reaction is substantially complete, the product of formula (7) is isolated conventionally, for example by evaporation of the solvents under reduced pressure, and the residue is used in the next reaction with no further purification.

Step 4—Preparation of Formula (8)

The compound of formula (7) is reacted with aqueous ammonia in a polar solvent, for example suspended in methanol. The reaction is carried out at about room temperature, for about 1-3 days. When the reaction is substantially complete, the product of formula (8) is isolated conventionally, for example by chromatography over a silica gel column, eluting, for example, with a mixture of dichloromethane/methanol.

The compound of formula (3) may also be prepared by various methods. One preferred method is shown in Reaction Scheme III.

REACTION SCHEME III

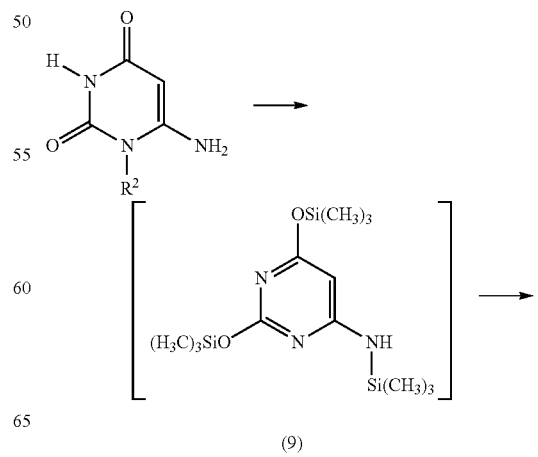

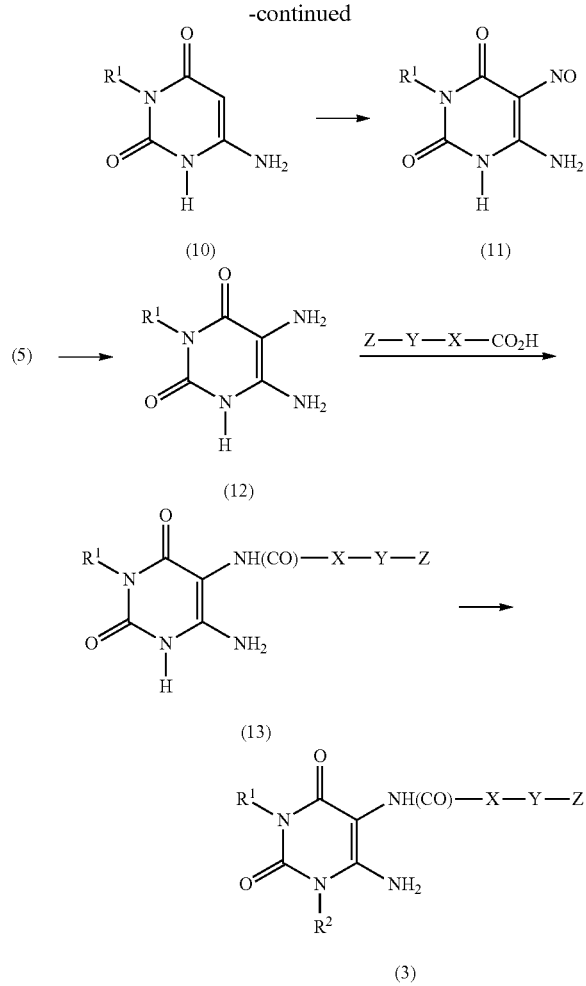

Step 1—Preparation of Formula (10)

The commercially available compound 6-aminouracil is first silylated, for example by reaction with excess hexamethyldisilazane as a solvent in the presence of a catalyst, for example ammonium sulfate. The reaction is carried out at about reflux temperature, for about 1-10 hours. When the reaction is substantially complete, the silylated compound thus produced is isolated conventionally, and then reacted with a compound of formula $R^1$Hal, where Hal is chloro, bromo, or iodo, preferably in the absence of a solvent. The reaction is carried out at about reflux, for about 4-48 hours, preferably about 12-16 hours. When the reaction is substantially complete, the product of formula (10) is isolated by conventional means.

Step 2—Preparation of Formula (11)

The compound of formula (10) is then dissolved in an aqueous acid, for example aqueous acetic acid, and reacted with sodium nitrite. The reaction is carried out at a temperature of about 20-50° C., preferably about 30° C., over about 30 minutes. When the reaction is substantially complete, the product of formula (11) is isolated by conventional means, for example by filtration.

Step 3—Preparation of Formula (12)

The compound of formula (11) is then reduced to a diamino derivative. In general, the compound of formula (11) is dissolved in aqueous ammonia, and then a reducing agent, for example sodium hydrosulfite, added. The reaction is conducted at a temperature of about 70° C. When the reaction is substantially complete, the product of formula (12) is isolated conventionally, for example by filtration of the cooled reaction mixture.

Step 4—Preparation of Formula (13)

The compound of formula (12) is then reacted with a carboxylic acid of the formula Z—Y—X—$CO_2$H in the presence of a carbodiimide, for example 1-(3-dimethylaminopropyl)-3-ethylcarbodiimide hydrochloride. The reaction is conducted at a temperature of about 20-30° C., for about 12-48 hours. When the reaction is substantially complete, the product of formula (13) is isolated conventionally, for example by filtration of the cooled reaction mixture.

Alternatively, the carboxylic acid of the formula Z—Y—X—$CO_2$H is converted to an acid halide of the formula Z—Y—X—C(O)L, where L is chloro or bromo, by reacting with a halogenating agent, for example thionyl chloride or thionyl bromide; alternatively, phosphorus pentachloride or phosphorus oxychloride may be used. The reaction is preferably conducted in the absence of a solvent, using excess halogenating agent, for example at a temperature of about 60-80° C., preferably about 70° C., for about 1-8 hours, preferably about 4 hours. When the reaction is substantially complete, the product of formula Z—Y—X—C(O)L is isolated conventionally, for example by removal of the excess halogenating agent under reduced pressure.

The product of the formula Z—Y—X—C(O)L is then reacted with a compound of formula (12) in an inert solvent, for example acetonitrile, in the presence of a tertiary base, for example triethylamine. The reaction is conducted at an initial temperature of about 0 C, and then allowed to warm to 20-30° C., preferably about room temperature, for about 12-48 hours, preferably about 16 hours. When the reaction is substantially complete, the product of formula (13) is isolated conventionally, for example by diluting the reaction mixture with water, filtering off the product, and washing the product with water followed by ether.

Step 5—Preparation of Formula (3)

The compound of formula (13) is reacted with a compound of formula $R^2$Hal, where Hal is chloro, bromo, or iodo, in the presence of a base, for example potassium carbonate. The reaction is carried out at about room temperature, for about 4-24 hour, preferably about 16 hours. When the reaction is substantially complete, the product of formula (3) is isolated conventionally, for example by evaporation of the solvents under reduced pressure, and the residue may be purified conventionally, or may be used in the next reaction with no further purification.

Another method of preparing a compound of formula (3) is shown in Reaction Scheme IV.

REACTION SCHEME IV

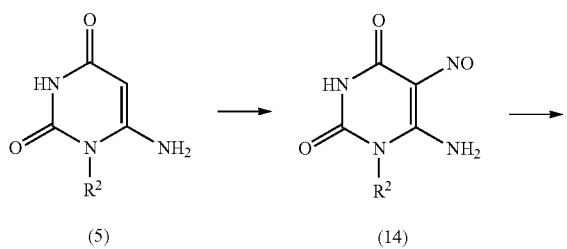

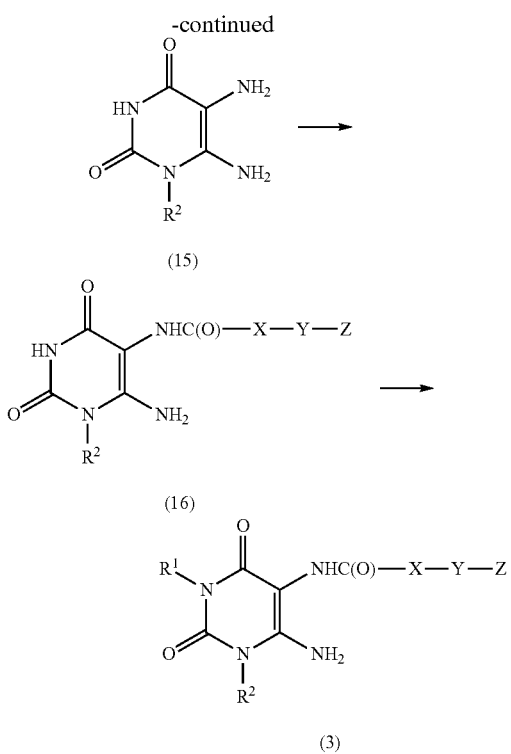

Step 1—Preparation of Formula (14)

The compound of formula (5) is then mixed with sodium nitrite in an aqueous acidic solvent, preferably acetic acid and water, for example 50% acetic acid/water. The reaction is carried out at a temperature of about 50-90° C., preferably about 70° C., for about 1 hour. When the reaction is substantially complete, the product of formula (14) is isolated by conventional means.

Alternatively, the reaction may be conducted in an aqueous solvent, for example dimethylformamide and water, and reacted with a strong acid, for example hydrochloric acid.

Step 3—Preparation of Formula (15)

The compound of formula (14) is then reduced to a diamino derivative. In general, the compound of formula (14) is dissolved in aqueous ammonia, and then a reducing agent, for example sodium hydrosulfite, added. The reaction is conducted at a temperature of about 70° C. When the reaction is substantially complete, the product of formula (15) is isolated conventionally, for example by filtration of the cooled reaction mixture.

Step 4—Preparation of Formula (16)

The compound of formula (15) is then reacted with a carboxylic acid of the formula Z—Y—X—CO$_2$H in the presence of a carbodiimide, for example 1-(3-dimethylaminopropyl)-3-ethylcarbodiimide hydrochloride. The reaction is conducted at a temperature of about 20-30° C., for about 12-48 hours, in an inert solvent, for example methanol. When the reaction is substantially complete, the product of formula (16) is isolated conventionally, for example by filtration of the cooled reaction mixture.

Alternatively, the carboxylic acid of the formula Z—Y—X—CO$_2$H is converted to an acid halide of the formula Z—Y—X—C(O)L, where L is chloro or bromo, by reacting with a halogenating agent, for example thionyl chloride or thionyl bromide; alternatively, phosphorus pentachloride or phosphorus oxychloride may be used. The reaction is preferably conducted in the absence of a solvent, using excess halogenating agent, for example at a temperature of about 60-80° C., preferably about 70° C., for about 1-8 hours, preferably about 4 hours. When the reaction is substantially complete, the product of formula Z—Y—X—C(O)L is isolated conventionally, for example by removal of the excess halogenating agent under reduced pressure.

The product of the formula Z—Y—X—C(O)L is then reacted with a compound of formula (15) in an inert solvent, for example acetonitrile, in the presence of a tertiary base, for example triethylamine. The reaction is conducted at an initial temperature of about 0 C, and then allowed to warm to 20-30° C., preferably about room temperature, for about 12-48 hours, preferably about 16 hours. When the reaction is substantially complete, the product of formula (16) is isolated conventionally, for example by diluting the reaction mixture with water, filtering off the product, and washing the product with water followed by ether.

Step 5—Preparation of Formula (3)

The compound of formula (16) is reacted with a compound of formula R$^1$Hal, where Hal is chloro, bromo, or iodo, in the presence of a base, for example potassium carbonate. The reaction is carried out at about 80° C., for about 4-24 hour, preferably about 16 hours. When the reaction is substantially complete, the product of formula (3) is isolated conventionally, for example by evaporation of the solvents under reduced pressure, and the residue may be purified conventionally, or may be used in the next reaction with no further purification.

An example of a synthesis of a compound of Z—Y—X—CO$_2$H in which X is pyrazol-1,4-yl, Y is methylene, and Z is 3-trifluoromethylphenyl, is shown in Reaction Scheme V.

REACTION SCHEME V

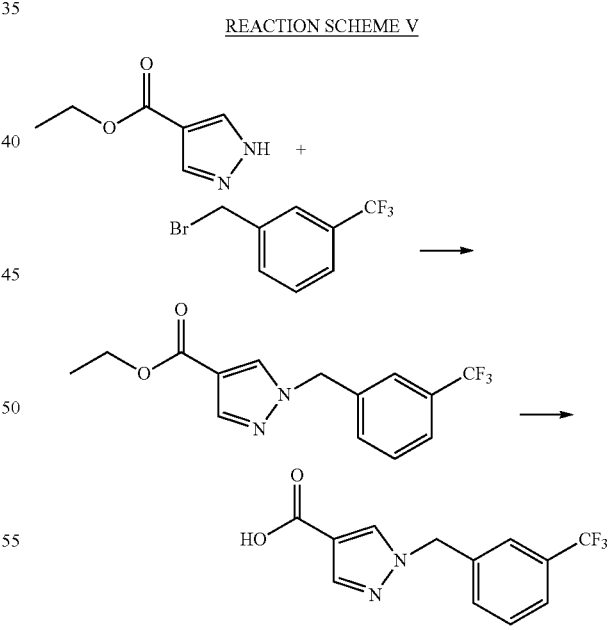

Ethyl pyrazole-4-carboxylate is reacted with 1-(bromomethyl)-3-(trifluoromethyl)benzene in acetone in the presence of potassium carbonate. The product, ethyl 1-{[3-(trifluoromethyl)phenyl]methyl}pyrazole-4-carboxylate, is then hydrolyzed with potassium hydroxide in methanol, to provide 1-{[3-(trifluoromethyl)phenyl]methyl}pyrazole-4-carboxylic acid.

Utility Testing and Administration

General Utility

The method and pharmaceutical compositions of the invention are effective in the prevention and treatment of hepatic disease such as hepatic fibrosis and/or hepatic inflammation in a mammal. Typical causes of hepatic disease include, but are not limited to, viral and alcoholic hepatitis, Wilson's disease, hemochromatosis, steatosis, and nonalcoholic steatohepatitis (NASH). Hepatic disease may also result as a consequence of surgical intervention, i.e., liver replacement or repair, or as a consequence of drug-induced liver damage.

Testing

Activity testing is conducted as described in those patents and patent applications referenced above, and in the Examples below, and by methods apparent to one skilled in the art.

Administration

The compounds of Formula I may be administered in either single or multiple doses by any of the accepted modes of administration of agents having similar utilities, for example as described in those patents and patent applications incorporated by reference, including buccal, intranasal, intra-arterial injection, intravenously, intraperitoneally, parenterally, intramuscularly, subcutaneously, orally, or as an inhalant.

Oral administration is the preferred route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Adenosine $A_{2B}$ receptor antagonists such as the compounds of Formula I are effective over a wide dosage range and is generally administered in a pharmaceutically effective amount. Typically, for oral administration, each dosage unit contains from 1 mg to 2 g of an adenosine $A_{2B}$ receptor antagonist, more commonly from 1 to 700 mg, and for parenteral administration, from 1 to 700 mg of an adenosine $A_{2B}$ receptor antagonist, more commonly about 2 to 200 mg. It will be understood, however, that the amount of the adenosine $A_{2B}$ receptor antagonist actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of a Compound of Formula (5)

A. Preparation of a Compound of Formula (5) in which $R^2$ is Ethyl

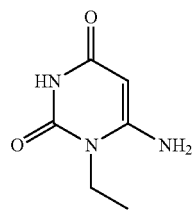

A solution of sodium ethoxide was prepared from sodium (4.8 g, 226 mmol) and dry ethanol (150 ml). To this solution was added amino-N-ethylamide (10 g, 113 m mol) and ethyl cyanoacetate (12.8 g, 113 mmol). This reaction mixture was stirred at reflux for 6 hours, cooled, and solvent removed from the reaction mixture under reduced pressure. The residue was dissolved in water (50 ml), and the pH adjusted to 7 with hydrochloric acid. The mixture was allowed to stand overnight at 0° C., and the precipitate filtered off, washed with water and air-dried, to provide 6-amino-1-ethyl-1,3-dihydropyrimidine-2,4-dione, a compound of formula (5).

$^1$H-NMR (DMSO-d6) δ 10.29 (s, 1H), 6.79 (s, 2H), 4.51 (s, 1H), 3.74-3.79 (m, 2H), 1.07 (t, 3H, J=7.03 Hz); MS m/z 155.98 (M$^+$), 177.99 (M$^+$+Na)

B. Preparation of a Compound of Formula (5) in which $R^2$ is Methyl

Similarly, following the procedure of Example 1A, but replacing amino-N-ethylamide with amino-N-methylamide, 6-amino-1-methyl-1,3-dihydropyrimidine-2,4-dione was prepared.

C. Preparation of a Compound of Formula (5) Varying $R^2$

Similarly, following the procedure of Example 1A, but replacing amino-N-ethylamide with other compounds of formula (4), other compounds of formula (5) are prepared.

Example 2

Preparation of a Compound of Formula (6)

A. Preparation of a Compound of Formula (6) in which $R^2$ is Ethyl

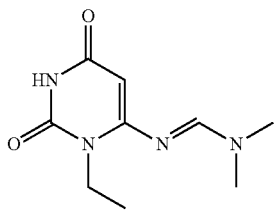

A suspension of 6-amino-1-ethyl-1,3-dihydropyrimidine-2,4-dione (0.77 g, 5 mmol) in anhydrous N,N-dimethylacetamide (25 ml) and N,N-dimethylformamide dimethylacetal (2.7 ml, 20 mmol) and was warmed at 40° C. for 90 minutes. Solvent was then removed under reduced pressure, and the residue triturated with ethanol, filtered, and washed with ethanol, to provide 6-[2-(dimethylamino)-1-azavinyl]-1-ethyl-1,3-dihydropyrimidine-2,4-dione, a compound of formula (6).

$^1$H-NMR (DMSO-d6) δ 10.62 (s, 1H), 8.08 (s, 1H), 4.99 (s, 1H), 3.88-3.95 (m, 2H), 3.13 (s, 3H), 2.99 (s, 3H), 1.07 (t, 3H, J=7.03 Hz); MS m/z 210.86 (M$^+$), 232.87 (M$^+$+Na)

B. Preparation of a Compound of Formula (6) in which $R^2$ is Methyl

Similarly, following the procedure of Example 2A, but replacing 6-amino-1-ethyl-1,3-dihydropyrimidine-2,4-dione with 6-amino-1-methyl-1,3-dihydropyrimidine-2,4-dione, 6-[2-(dimethylamino)-1-azavinyl]-1-methyl-1,3-dihydropyrimidine-2,4-dione was prepared.

C. Preparation of a Compound of Formula (6) Varying $R^2$

Similarly, following the procedure of Example 2A, but replacing 6-amino-1-ethyl-1,3-dihydropyrimidine-2,4-dione with other compounds of formula (5), other compounds of formula (6) are prepared.

Example 3

Preparation of a Compound of Formula (7)

A. Preparation of a Compound of Formula (7) in which $R^1$ is n-Propyl and $R^2$ is Ethyl

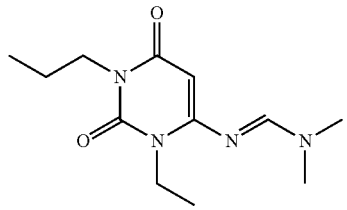

A mixture of a solution of 6-[2-(dimethylamino)-1-azavinyl]-1-ethyl-1,3-dihydropyrimidine-2,4-dione (1.5 g, 7.1 mmol) in dimethylformamide (25 ml), potassium carbonate (1.5 g, 11 mmol) and n-propyl iodide (1.54 g, 11 mmol) was stirred at 80° C. for 5 hours. The reaction mixture was cooled to room temperature, filtered, the solvents were evaporated and the product of formula (7), 6-[2-(dimethylamino)-1-azayinyl]-1-ethyl-3-propyl-1,3-dihydropyrimidine-2,4-dione, was used as such in the next reaction.

B. Preparation of a Compound of Formula (7), Varying $R^1$ and $R^2$

Similarly, following the procedure of Example 3A, but replacing 6-[2-(dimethylamino)-1-azavinyl]-1-ethyl-1,3-dihydropyrimidine-2,4-dione with other compounds of formula (6), the following compounds of formula (7) were prepared:

6-[2-(dimethylamino)-1-azavinyl]-1-methyl-3-propyl-1,3-dihydropyrimidine-2,4-dione.

6-[2-(dimethylamino)-1-azavinyl]-1-methyl-3-cyclopropylmethyl-1,3-dihydropyrimidine-2,4-dione;

6-[2-(dimethylamino)-1-azavinyl]-1-ethyl-3-cyclopropylmethyl-1,3-dihydropyrimidine-2,4-dione;

6-[2-(dimethylamino)-1-azavinyl]-1-methyl-3-(2-methylpropyl)-1,3-dihydropyrimidine-2,4-dione; and 6-[2-(dimethylamino)-1-azavinyl]-1-ethyl-3-(2-methylpropyl)-1,3-dihydropyrimidine-2,4-dione.

C. Preparation of a Compound of Formula (7), Varying $R^1$ and $R^2$

Similarly, following the procedure of Example 3A, but replacing 6-[2-(dimethylamino)-1-azavinyl]-1-ethyl-1,3-dihydropyrimidine-2,4-dione with other compounds of formula (6), other compounds of formula (7) are prepared.

Example 4

Preparation of a Compound of Formula (8)

A. Preparation of a Compound of Formula (8) in which $R^1$ is n-Propyl and $R^2$ is Ethyl

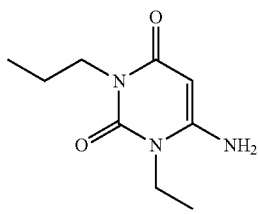

A solution of 6-[2-(dimethylamino)-1-azavinyl]-1-ethyl-3-propyl-1,3-dihydropyrimidine-2,4-dione (2.1 g) was dissolved in a mixture of methanol (10 ml) and 28% aqueous ammonia solution (20 ml), and stirred for 72 hours at room temperature. Solvent was then removed under reduced pressure, and the residue purified by chromatography on a silica gel column, eluting with a mixture of dichloromethane/methanol (15/1), to provide 6-amino-1-ethyl-3-propyl-1,3-dihydropyrimidine-2,4-dione, a compound of formula (8).

$^1$H-NMR (DMSO-d6) δ 6.80 (s, 2H), 4.64 (s, 1H), 3.79-3.84 (m, 2H), 3.63-3.67 (m, 2H), 1.41-1.51 (m, 2H), 1.09 (t, 3H, J=7.03 Hz), 0.80 (t, 3H, J=7.42 Hz); MS m/z 197.82

B. Preparation of a Compound of Formula (8), Varying $R^1$ and $R^2$

Similarly, following the procedure of Example 4A, but replacing 6-[2-(dimethylamino)-1-azavinyl]-1-ethyl-3-propyl-1,3-dihydropyrimidine-2,4-dione with other compounds of formula (7), the following compounds of formula (8) were prepared:

6-amino-1-methyl-3-propyl-1,3-dihydropyrimidine-2,4-dione;

6-amino-1-methyl-3-cyclopropylmethyl-1,3-dihydropyrimidine-2,4-dione;

6-amino-1-ethyl-3-cyclopropylmethyl-1,3-dihydropyrimidine-2,4-dione;

6-amino-1-methyl-3-(2-methylpropyl)-1,3-dihydropyrimidine-2,4-dione; and 6-amino-1-ethyl-3-(2-methylpropyl)-1,3-dihydropyrimidine-2,4-dione.

C. Preparation of a Compound of Formula (7) Varying $R^1$ and $R^2$

Similarly, following the procedure of Example 4A, but replacing 6-[2-(dimethylamino)-1-azavinyl]-1-ethyl-3-propyl-1,3-dihydropyrimidine-2,4-dione with other compounds of formula (7), other compounds of formula (8) are prepared.

Example 5

Preparation of a Compound of Formula (1)

A. Preparation of a Compound of Formula (1) in which $R^1$ is n-Propyl and $R^2$ is Ethyl

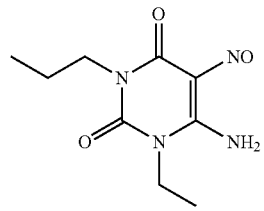

To a solution of 6-amino-1-ethyl-3-propyl-1,3-dihydropyrimidine-2,4-dione (1.4 g, 7.1 mmol) in a mixture of 50% acetic acid/water (35 ml) was added sodium nitrite (2 g, 28.4 mmol) in portions over a period of 10 minutes. The mixture was stirred at 70° C. for 1 hour, then the reaction mixture concentrated to a low volume under reduced pressure. The solid was filtered off, and washed with water, to provide 6-amino-1-ethyl-5-nitroso-3-propyl-1,3-dihydropyrimidine-2,4-dione, a compound of formula (1).

MS m/z 227.05 (M$^+$), 249.08 (M$^+$+Na)

B. Preparation of a Compound of Formula (1), Varying $R^1$ and $R^2$

Similarly, following the procedure of Example 5A, but replacing 6-amino-1-ethyl-3-propyl-1,3-dihydropyrimidine-2,4-dione with other compounds of formula (8), the following compounds of formula (1) were prepared:

6-amino-1-methyl-5-nitroso-3-propyl-1,3-dihydropyrimidine-2,4-dione;

6-amino-1 ethyl-3-cyclopropylmethyl-5-nitroso-1,3-dihydropyrimidine-2,4-dione;

6-amino-1-ethyl-3-cyclopropylmethyl-5-nitroso-1,3-dihydropyrimidine-2,4-dione;

6-amino-1-methyl-3-(2-methylpropyl)-5-nitroso-1,3-dihydropyrimidine-2,4-dione; and 6-amino-1-ethyl-3-(2-methylpropy)-5-nitroso-1,3-dihydropyrimidine-2,4-dione.

C. Preparation of a Compound of Formula (1) Varying $R^1$ and $R^2$

Similarly, following the procedure of Example 5A, but replacing 6-amino-1-ethyl-3-propyl-1,3-dihydropyrimidine-2,4-dione with other compounds of formula (8), other compounds of formula (1) are prepared.

Example 6

Preparation of a Compound of Formula (2)

A. Preparation of a Compound of Formula (2) in which $R^1$ is n-Propyl and $R^2$ is Ethyl

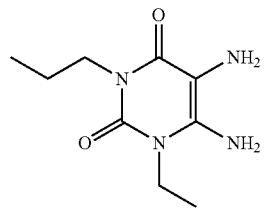

To a solution of 6-amino-1-ethyl-5-nitroso-3-propyl-1,3-dihydropyrimidine-2,4-dione (300 mg) in methanol (10 ml) was added 10% palladium on carbon catalyst (50 mg), and the mixture was hydrogenated under hydrogen at 30 psi for 2 hours. The mixture was filtered through celite, and solvent was removed from the filtrate under reduced pressure, to provide 5,6-diamino-1-ethyl-3-propyl-1,3-dihydropyrimidine-2,4-dione, a compound of formula (2).

MS m/z 213.03 (M+), 235.06 (M++Na)

B. Preparation of a Compound of Formula (2), Varying $R^1$ and $R^2$

Similarly, following the procedure of Example 6A, but replacing 6-amino-1-ethyl-5-nitroso-3-propyl-1,3-dihydropyrimidine-2,4-dione with other compounds of formula (1), the following compounds of formula (2) were prepared:

5,6-diamino-1-methyl-3-propyl-1,3-dihydropyrimidine-2,4-dione;
5,6-diamino-1-methyl-3-cyclopropylmethyl-1,3-dihydropyrimidine-2,4-dione;
5,6-diamino-1-ethyl-3-cyclopropylmethyl-1,3-dihydropyrimidine-2,4-dione;
5,6-amino-1-methyl-3-(2-methylpropyl)-1,3-dihydropyrimidine-2,4-dione; and
5,6-diamino-1-ethyl-3-(2-methylpropyl)-1,3-dihydropyrimidine-2,4-dione.

C. Preparation of a Compound of Formula (2) Varying $R^1$ and $R^2$

Similarly, following the procedure of Example 6A, but replacing 6-amino-1-ethyl-5-nitroso-3-propyl-1,3-dihydropyrimidine-2,4-dione with other compounds of formula (1), other compounds of formula (2) are prepared.

Example 7

Preparation of a Compound of Formula (3)

A. Preparation of a Compound of Formula (3) in which $R^1$ is n-Propyl, $R^2$ is Ethyl, X is 1,4-Pyrazolyl, Y is Methylene, and Z is 3-Trifluoromethylphenyl

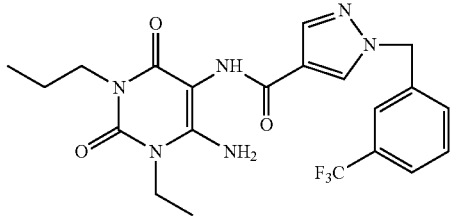

To a mixture of 5,6-diamino-1-ethyl-3-propyl-1,3-dihydropyrimidine-2,4-dione (100 mg, 0.47 mmol) and 1-{[3-(trifluoromethyl)phenyl]methyl}pyrazole-4-carboxylic acid (0.151 g, 0.56 mmol) in methanol (10 ml) was added 1-(3-dimethylaminopropyl)-3-ethylcarbodiimide hydrochloride (0.135 g, 0.7 mmol), and the reaction mixture was stirred overnight at room temperature. The solvent was removed under reduced pressure, and the residue purified using Bistag, eluting with 10% methanol/methylene chloride, to provide N-(6-amino-1-ethyl-2,4-dioxo-3-propyl(1,3-dihydropyrimidin-5-yl))(1-{[3-(trifluoromethyl)phenyl]methyl}-pyrazol-4-yl)carboxamide.

$^1$H-NMR (DMSO-d6) δ 8.59 (s, 1H), 8.02 (s, 1H), 7.59-7.71 (m, 4H), 6.71 (s, 2H), 5.51 (s, 2H), 3.91-3.96 (m, 2H), 3.70-3.75 (m, 2H), 1.47-1.55 (m, 2H), 1.14 (t, 3H, J=7.03 Hz), 0.85 (t, 3H, J=7.42 Hz).

B. Preparation of a Compound of Formula (3), Varying $R^1$, $R^2$, X, Y, and Z

Similarly, following the procedure of Example 7A or 7B, but optionally replacing 5,6-diamino-1-ethyl-3-propyl-1,3-dihydropyrimidine-2,4-dione with other compounds of formula (2), and optionally replacing 1-{[3-(trifluoromethyl)phenyl]methyl}pyrazole-4-carboxylic acid with other compounds of formula Z—Y—X—CO$_2$H, the following compounds of formula (3) were prepared:

N-(6-amino-1-methyl-2,4-dioxo-3-propyl(1,3-dihydropyrimidin-5-yl))(1-{[3-(trifluoromethyl)phenyl]methyl}-pyrazol-4-yl)carboxamide;
N-(6-amino-1-methyl-2,4-dioxo-3-cyclopropylmethyl(1,3-dihydropyrimidin-5-yl))(1-{[3-(trifluoromethyl)phenyl]methyl}-pyrazol-4-yl)carboxamide;
N-(6-amino-1-ethyl-2,4-dioxo-3-cyclopropylmethyl (1,3-dihydropyrimidin-5-yl))(1-{[3-(trifluromethyl)phenyl]methyl}-pyrazol-4-yl)carboxamide;
N-(6-amino-1-methyl-2,4-dioxo-3-ethyl(1,3-dihydropyrimidin-5-yl))(1-{[3-fluorophenyl]methyl}-pyrazol-4-yl)carboxamide;
N-(6-amino-1-methyl-2,4-dioxo-3-cyclopropylmethyl(1,3-dihydropyrimidin-5-yl))(1-{[3-fluorophenyl]methyl}-pyrazol-4-yl)carboxamide;
N-(6-amino-1-ethyl-2,4-dioxo-3-cyclopropylmethyl(1,3-dihydropyrimidin-5-yl))(1-{[3-fluorophenyl]methyl}-pyrazol-4-yl)carboxamide;
N-[6-amino-3-(cyclopropylmethyl)-1-methyl-2,4-dioxo(1,3-dihydropyrimidin-5-yl)][1-benzylpyrazol-4-yl]carboxamide;
N-(6-amino-1-methyl-2,4-dioxo-3-cyclopropylmethyl(1,3-dihydropyrimidin-5-yl))(1-{[3-cyanophenyl]methyl}-pyrazol-4-yl)carboxamide;
[1-(2-(1H-1,2,3,4-tetraazol-5-yl)ethyl)pyrazol-4-yl]-N-[6-amino-3-(cyclopropylmethyl)-1-methyl-2,4-dioxo(1,3-dihydropyrimidin-5-yl)]carboxamide;
N-[6-amino-3-(cyclopropylmethyl)-1-ethyl-2,4-dioxo(1,3-dihydropyrimidin-5-yl)](1-{[6-(trifluoromethyl)(3-pyridyl)]methyl}pyrazol-4-yl)carboxamide;
N-[6-amino-3-propyl)-1-ethyl-2,4-dioxo(1,3-dihydropyrimidin-5-yl)](1-{(2-pyridyl)]methyl}pyrazol-4-yl)carboxamide;
N-[6-amino-3-(2-methylpropyl)-1-methyl-2,4-dioxo(1,3-dihydropyrimidin-5-yl)][1-benzylpyrazol-4-yl]carboxamide;
N-[6-amino-3-(2-methylpropyl)-1-methyl-2,4-dioxo(1,3-dihydropyrimidin-5-yl)][1-{[3-fluorophenyl]methyl}pyrazol-4-yl]carboxamide;
N-[6-amino-3-(2-methylpropyl)-1-ethyl-2,4-dioxo(1,3-dihydropyrimidin-5-yl)][1-{[3-fluorophenyl]methyl}pyrazol-4-yl]carboxamide;
N-[6-amino-3-(2-methylpropyl)-1-methyl-2,4-dioxo(1,3-dihydropyrimidin-5-yl)][1-{[3-(trifluoromethyl)phenyl]methyl}pyrazol-4-yl]carboxamide; and
N-[6-amino-3-(2-methylpropyl)-1-ethyl-2,4-dioxo(1,3-dihydropyrimidin-5-yl)](1-{[6-(trifluoromethyl)(3-pyridyl)]methyl}pyrazol-4-yl)carboxamide.

C. Preparation of a Compound of Formula (2) Varying $R^1$ and $R^2$

Similarly, following the procedure of Example 7A, but optionally replacing 5,6-diamino-1-ethyl-3-propyl-1,3-dihydropyrimidine-2,4-dione with other compounds of formula (2), and optionally replacing 1-{[3-(trifluoromethyl)phenyl]methyl}pyrazole-4-carboxylic acid with other compounds of formula Z—Y—X—CO$_2$H, other compounds of formula (3) are prepared.

Example 8

Preparation of a Compound of Formula I

A. Preparation of a Compound of Formula I in which $R^1$ is n-Propyl, $R^2$ is Ethyl, X is 1,4-Pyrazolyl, Y is Methylene, and Z is 3-Trifluoromethylphenyl

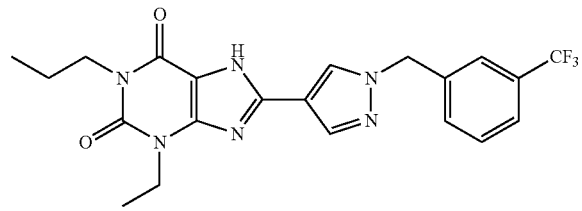

A mixture of N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide (80 mg, 0.17 mmol), 10% aqueous sodium hydroxide (5 ml), and methanol (5 ml) was stirred at 100° C. for 2 hours. The mixture was cooled, methanol removed under reduced pressure, and the residue diluted with water and acidified with hydrochloric acid. The precipitate was filtered off, washed with water, then methanol, to provide 3-ethyl-1-propyl-8-(1-{[3-(trifluoromethyl)phenyl]methyl}pyrazol-4-yl)-1,3,7-trihydropurine-2,6-dione, a compound of Formula I.

$^1$H-NMR (DMSO-d6) δ 8.57 (s, 1H), 8.15 (s, 1H), 7.60-7.75 (m, 4H), 5.54 (s, 2H), 4.05-4.50 (m, 2H), 3.87-3.91 (m, 2H), 1.55-1.64 (m, 2H), 1.25 (t, 3H, J=7.03 Hz), 0.90 (t, 3H, J=7.42 Hz); MS m/z 447.2 (M$^+$).

B. Preparation of a Compound of Formula I, Varying $R^1$, $R^2$, X, Y, and Z

Similarly, following the procedure of Example 8A, but replacing N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide with other compounds of formula (3), the following compounds of Formula I were prepared:

1-cyclopropylmethyl-3-methyl-8-[1-(phenylmethyl)pyrazol-4-yl]-1,3,7-trihydropurine-2,6-dione;
1-cyclopropylmethyl-3-methyl-8-{1-[(3-trifluoromethylphenyl)methyl]pyrazol-4-yl}-1,3,7-trihydropurine-2,6-dione;
1-cyclopropylmethyl-3-ethyl-8-{1-[(3-trifluoromethylphenyl)methyl]pyrazol-4-yl}-1,3,7-trihydropurine-2,6-dione;
1-cyclopropylmethyl-3-methyl-8-{1-[(3-fluorophenyl)methyl]pyrazol-4-yl}-1,3,7-trihydropurine-2,6-dione;
1-cyclopropylmethyl-3-ethyl-8-{1-[(3-fluorophenyl)methyl]pyrazol-4-yl}-1,3,7-trihydropurine-2,6-dione;
1-cyclopropylmethyl-3-ethyl-8-(1-{[6-(trifluoromethyl)(3-pyridyl)]methyl}pyrazol-4-yl)-1,3,7-trihydropurine-2,6-dione;
3-({4-[1-(cyclopropylmethyl)-3-methyl-2,6-dioxo-1,3,7-trihydropurin-8-yl]pyrazolyl}methyl)benzenecarbonitrile;
8-[1-(2-(1H-1,2,3,4-tetraazol-5-yl)ethyl)pyrazol-4-yl]-3-methyl-1-cyclopropylmethyl-1,3,7-trihydropurine-2,6-dione;
1-(2-methylpropyl)-3-methyl-8-[1-benzylpyrazol-4-yl]-1,3,7-trihydropurine-2,6-dione;
1-(2-methylpropyl)-3-ethyl-8-{1-[(3-fluorophenyl)methyl]pyrazol-4-yl}-1,3,7-trihydropurine-2,6-dione;
1-(2-methylpropyl)-3-methyl-8-{1-[(3-trifluoromethylphenyl)methyl]pyrazol-4-yl}-1,3,7-trihydropurine-2,6-dione;
1-(2-methylpropyl)-3-methyl-8-{1-[(3-fluorophenyl)methyl]pyrazol-4-yl}-1,3,7-trihydropurine-2,6-dione;
3-ethyl-1-(2-methylpropyl)-8-(1-{[6-(trifluoromethyl)(3-pyridyl)]methyl}pyrazol-4-yl)-1,3,7-trihydropurine-2,6-dione;
1-ethyl-3-methyl-8-{1-[(3-fluorophenyl)methyl]pyrazol-4-yl}-1,3,7-trihydropurine-2,6-dione; and
3-ethyl-1-propyl-8-[1-(2-pyridylmethyl)pyrazol-4-yl]-1,3,7-trihydropurine-2,6-dione.

C. Preparation of a Compound of Formula I, Varying $R^1$, $R^2$, X, Y, and Z

Similarly, following the procedure of Example 8A, but replacing N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide with other compounds of formula (3), other compounds of Formula I are prepared.

Example 9

Preparation of a Compound of Formula (10)

A. Preparation of a Compound of Formula (10) in which $R^1$ is n-Propyl

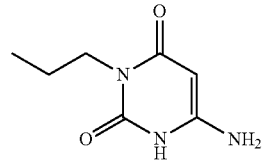

A mixture of 6-aminouracil (5.08 g, 40 mmol), hexamethyldisilazane (50 ml), and ammonium sulfate (260 mg, 1.96 mmol) was refluxed for 12 hours. After cooling, the solid was filtered off, and solvent was removed from the filtrate under reduced pressure to provide the trimethylsilylated derivative of 6-aminouracil.

The product was dissolved in toluene (1.5 ml), and iodopropane (7.8 ml, 80 mmol) and heated in an oil bath at 120° C. for 2 hours. The reaction mixture was then cooled to 0° C., and saturated aqueous sodium bicarbonate added slowly. The resulting precipitate was filtered off, and washed sequentially with water, toluene, and ether, to provide 6-amino-3-propyl-1,3-dihydropyrimidine-2,4-dione, a compound of formula (10), which was used in the next reaction with no further purification.

$^1$H-NMR (DMSO-d6) δ 10.34 (s, 1H), 6.16 (s, 2H), 4.54 (s, 1H), 3.57-3.62 (m, 2H), 1.41-1.51 (m, 2H), 0.80 (t, 3H, J=7.43 Hz).

B. Preparation of a Compound of Formula (10), Varying $R^1$

Similarly, following the procedure of Example 9A, but replacing iodopropane with other alkyl halides of formula $R^1$Hal, other compounds of formula (10) are prepared, including:

6-amino-3-cyclopropylmethyl-1,3-dihydropyrimidine-2,4-dione; and 6-amino-3-(2-methylpropyl)-1,3-dihydropyrimidine-2,4-dione.

Example 10

Preparation of a Compound of Formula (11)

A. Preparation of a Compound of Formula (10) in which $R^1$ is n-Propyl

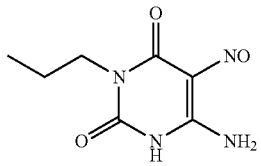

To a solution of 6-amino-3-propyl-1,3-dihydropyrimidine-2,4-dione (5.6 g) in a mixture of 50% acetic acid/water (160 ml) at 70° C. was added sodium nitrite (4.5 g) in portions over a period of 15 minutes. The mixture was stirred at 70° C. for 45 minutes, then the reaction mixture concentrated to a low volume under reduced pressure. The solid was filtered off, and washed with water, to provide 6-amino-5-nitroso-3-propyl-1,3-dihydropyrimidine-2,4-dione, a compound of formula (11).

$^1$H-NMR (DMSO-d6) δ 11.42 (s, 1H), 7.98 (s, 1H), 3.77-3.81 (m, 2H), 3.33 (s, 1H), 1.55-1.64 (m, 2H), 0.89 (t, 31-1, J=7.43 Hz); MS m/z 198.78 (M$^+$), 220.78 (M$^+$+Na)

B. Preparation of a Compound of Formula (11), Varying $R^1$

Similarly, following the procedure of Example 10A, but replacing 6-amino-3-propyl-1,3-dihydropyrimidine-2,4-dione with other compounds of formula (10), other compounds of formula (11) are prepared, including:

6-amino-5-nitroso-3-cyclopropylmethyl-1,3-dihydropyrimidine-2,4-dione; and 6-amino-5-nitroso-3-(2-methylpropyl)-1,3-dihydropyrimidine-2,4-dione.

Example 11

Preparation of a Compound of Formula (12)

A. Preparation of a Compound of Formula (12) in which $R^1$ is n-Propyl

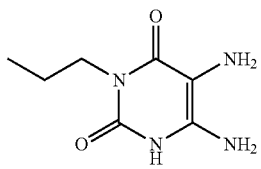

To a solution of 6-amino-5-nitroso-3-propyl-1,3-dihydropyrimidine-2,4-dione (5.4 g, 27 mmol) in 12.5% aqueous ammonia (135 ml) at 70° C. was added sodium dithionite (Na$_2$S$_2$O$_4$, 9.45 g, 54 mmol) in portions over 15 minutes, and the mixture was stirred for 20 minutes. The solution was concentrated under reduced pressure, cooled to 5° C., the precipitate filtered off, and washed with cold water, to provide 5,6-diamino-3-propyl-1,3-dihydropyrimidine-2,4-dione, a compound of formula (12).

$^1$H-NMR (DMSO-d6) δ 0.81 (t, 3H, J=7.43 Hz), 1.43-1.52 (m, 2H), 3.63-3.67 (m, 2H), 5.56 (s, 2H); MS m/z 184.95 (M$^+$) 206.96 (M$^+$+Na)

B. Preparation of a Compound of Formula (12), Varying $R^1$

Similarly, following the procedure of Example 11A, but replacing 6-amino-3-propyl-1,3-dihydropyrimidine-2,4-dione with other compounds of formula (11), other compounds of formula (12) are prepared, including:

5,6-diamino-3-cyclopropylmethyl-1,3-dihydropyrimidine-2,4-dione; and 5,6-diamino-3-(2-methylpropyl)-1,3-dihydropyrimidine-2,4-dione.

Example 12

Preparation of a Compound of Formula (13)

A. Preparation of a Compound of Formula (13) in which $R^1$ is n-Propyl, X is 1,4-Pyrazolyl, Y is Methylene, and Z is 3-Trifluoromethylphenyl

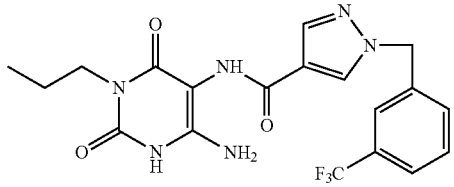

To a mixture of 5,6-diamino-3-propyl-1,3-dihydropyrimidine-2,4-dione (2.3 g, 126 mmol) and 1-{[3-(trifluoromethyl)phenyl]methyl}pyrazole-4-carboxylic acid (3.79 g, 14 mmol) in methanol (50 ml) was added 1-(3-dimethylaminopropyl)-3-ethylcarbodiimide hydrochloride (2.67 g, 14 mmol), and the reaction mixture was stirred for 3 days at room temperature (although less time is acceptable). The precipitate was filtered off, and was washed sequentially with water, and methanol. The product was dried under vacuum to provide N-(6-amino-2,4-dioxo-3-propyl(1,3-dihydropyrimidin-5-yl))(1-{[3-(trifluoromethyl)phenyl]methyl}pyrazol-4-yl)carboxamide, a compound of formula (13).

$^1$H-NMR (DMSO-d6) δ 10.44 (s, 1H), 8.56 (s, 1H), 8.37 (s, 1H), 8.00 (s, 1H), 7.56-7.71 (m, 3H), 6.02 (s, 1H), 5.49 (s, 2H), 3.62-3.66 (m, 2H), 1.44-1.53 (m, 2H), 0.82 (t, 3H, J=7.43 Hz); MS m/z 458.92 (M$^+$+Na).

B. Alternative Preparation of a Compound of Formula (3) in which $R^1$ is n-Propyl, X is 1,4-Pyrazolyl, Y is Methylene, and Z is 3-Trifluoromethylphenyl A solution of 1-{[3-(trifluoromethyl)phenyl]methyl}pyrazole-4-carboxylic acid (1 g, 3.7 mmol) in thionyl chloride (1 ml) was heated at 70° C. for 4 hours. Excess thionyl chloride was distilled off, and the residue treated with methylene chloride/hexanes. The solvent was removed under reduced pressure, and the residue dissolved in acetonitrile. This solution was added to a suspension of 5,6-diamino-3-propyl-1,3-dihydropyrimidine-2,4-dione (2.3 g, 126 mmol) and triethylamine (1 ml) in acetonitrile (20 ml) at 0° C., and stirred for 16 hours. The reaction mixture was quenched with water (5 ml), acidified with hydrochloric acid, stirred for 30 minutes, and the precipitate filtered off. The product was washed with ether, to provide N-(6-amino-2,4-dioxo-3-propyl(1,3-dihydropyrimidin-5-yl))(1-{[3-(trifluoromethyl)phenyl]methyl}pyrazol-4-yl)carboxamide, a compound of formula (13).

C. Preparation of a Compound of Formula (13), Varying $R^1$, X, Y, and Z

Similarly, following the procedure of Example 12A or 12B, but optionally replacing 6-amino-3-propyl-1,3-dihydropyrimidine-2,4-dione with other compounds of formula (12), and optionally replacing 1-{[3-(trifluoromethyl)phenyl]methyl}pyrazole-4-carboxylic acid with other compounds of formula Z—Y—X—$CO_2$H, other compounds of formula (13) are prepared, including:

N-(6-amino-2,4-dioxo-3-cyclopropylmethyl(1,3-dihydropyrimidin-5-yl))(1-{[3-(trifluoromethyl)phenyl]methyl}pyrazol-4-yl)carboxamide;

N-(6-amino-2,4-dioxo-3-(2-methylpropyl)(1,3-dihydropyrimidin-5-yl))(1-{[3-(trifluoromethyl)phenyl]methyl}pyrazol-4-yl)carboxamide;

N-(6-amino-2,4-dioxo-3-propyl(1,3-dihydropyrimidin-5-yl))(1-{[3-fluorophenyl]methyl}pyrazol-4-yl)carboxamide;

N-(6-amino-2,4-dioxo-3-cyclopropylmethyl(1,3-dihydropyrimidin-5-yl))(1-{[3-fluorophenyl]methyl}pyrazol-4-yl)carboxamide;

N-(6-amino-2,4-dioxo-3-(2-methylpropyl)(1,3-dihydropyrimidin-5-yl))(1-{[3-fluorophenyl]methyl}pyrazol-4-yl)carboxamide;

N-(6-amino-2,4-dioxo-3-propyl(1,3-dihydropyrimidin-5-yl))(1-[1-benzyl]pyrazol-4-yl)carboxamide;

N-(6-amino-2,4-dioxo-3-cyclopropylmethyl(1,3-dihydropyrimidin-5-yl))(1-[1-benzyl]pyrazol-4-yl)carboxamide;

N-(6-amino-2,4-dioxo-3-(2-methylpropyl)(1,3-dihydropyrimidin-5-yl))(1-[1-benzyl]pyrazol-4-yl)carboxamide;

N-(6-amino-2,4-dioxo-3-propyl(1,3-dihydropyrimidin-5-yl))(1-{[3-cyanophenyl]methyl}pyrazol-4-yl)carboxamide;

N-(6-amino-2,4-dioxo-3-cyclopropylmethyl(1,3-dihydropyrimidin-5-yl))(1-{[3-cyanophenyl]methyl}pyrazol-4-yl)carboxamide;

N-(6-amino-2,4-dioxo-3-(2-methylpropyl)(1,3-dihydropyrimidin-5-yl))(1-{[3-cyanophenyl]methyl}pyrazol-4-yl)carboxamide;

N-(6-amino-2,4-dioxo-3-propyl(1,3-dihydropyrimidin-5-yl))(1-[1-(2-(1H-1,2,3,4-tetraazol-5-yl)ethyl)pyrazol-4-yl]carboxamide;

N-(6-amino-2,4-dioxo-3-cyclopropylmethyl (1,3-dihydropyrimidin-5-yl))(1-{[1-(2-(1H-1,2,3,4-tetraazol-5-yl)ethyl)pyrazol-4-yl)carboxamide;

N-(6-amino-2,4-dioxo-3-(2-methylpropyl)(1,3-dihydropyrimidin-5-yl))(1-[1-(2-(1H-1,2,3,4-tetraazol-5-yl)ethyl)pyrazol-4-yl)carboxamide;

N-(6-amino-2,4-dioxo-3-propyl(1,3-dihydropyrimidin-5-yl))(1-{[6-(trifluoromethyl)(3-pyridyl)]-methyl}pyrazol-4-yl)carboxamide;

N-(6-amino-2,4-dioxo-3-cyclopropylmethyl(1,3-dihydropyrimidin-5-yl))(1-{[6-(trifluoromethyl)(3-pyridyl)]methyl}pyrazol-4-yl)carboxamide; and N-(6-amino-2,4-dioxo-3-(2-methylpropyl)(1,3-dihydropyrimidin-5-yl))(1-{[6-(trifluoromethyl)(3-pyridyl)]methyl}pyrazol-4-yl)carboxamide.

Example 13

Preparation of a Compound of Formula (3)

A. Preparation of a Compound of Formula (3) in which $R^1$ is n-Propyl, $R^2$ is Ethyl, X is 1,4-Pyrazolyl, Y is Methylene, and Z is 3-Trifluoromethylphenyl

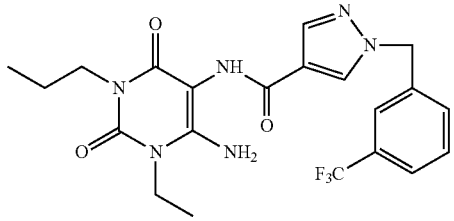

A mixture of a solution of N-(6-amino-2,4-dioxo-3-propyl(1,3-dihydropyrimidin-5-yl))(1-{[3-(trifluoromethyl)-phenyl]methyl}pyrazol-3-yl)carboxamide (872 mg, 2 mmol) in dimethylformamide (10 ml), potassium carbonate (552 mg, 4 mmol) and ethyl iodide (0.24 ml, 3 mmol) was stirred at room temperature overnight. The reaction mixture was filtered, and the solvent was evaporated from the filtrate under reduced pressure. The residue was stirred with water for two hours at room temperature, and the precipitate filtered off, washed with water, and then dissolved in methanol. The solvent was then removed under reduced pressure to provide N-(6-amino-1-ethyl-2,4-dioxo-3-propyl(1,3-dihydropyrimidin-5-yl))(1-{[3-(trifluoromethyl)phenyl]methyl}pyrazol-4-yl)carboxamide, a compound of formula (3).

$^1$H-NMR (DMSO-d6): δ 8.58 (s, 1H), 8.39 (s, 1H), 8.01 (s, 1H), 7.72-7.50 (m, 4H), 6.71 (s, 2H), 5.51 (s, 2H), 4.0-3.82 (m, 2H), 3.77-3.65 (m, 2H), 1.60-1.50 (m, 2H), 1.13 (t, 3H, J=6.8 Hz), 0.84 (t, 3H, J=7.2 Hz); MS m/z 462.9 (M$^-$)

B. Preparation of a Compound of Formula (13), Varying $R^1$, X, Y, and Z

Similarly, following the procedure of Example 13A, but replacing N-(6-amino-2,4-dioxo-3-propyl(1,3-dihydropyrimidin-5-yl))(1-{[3-(trifluoromethyl)phenyl]methyl}pyrazol-3-yl)carboxamide with other compounds of formula (13), other compounds of formula (3) are prepared, including:

N-(6-amino-1-methyl-2,4-dioxo-3-propyl(1,3-dihydropyrimidin-5-yl))(1-{[3-(trifluoromethyl)phenyl]methyl}-pyrazol-4-yl)carboxamide;

N-(6-amino-1-methyl-2,4-dioxo-3-cyclopropylmethyl(1,3-dihydropyrimidin-5-yl))(1-{[3-(trifluoromethyl)phenyl]methyl}-pyrazol-4-yl)carboxamide;

N-(6-amino-1-ethyl-2,4-dioxo-3-cyclopropylmethyl (1,3-dihydropyrimidin-5-yl))(1-{[3-(trifluoromethyl)phenyl]methyl}-pyrazol-4-yl)carboxamide;

N-(6-amino-1-methyl-2,4-dioxo-3-ethyl(1,3-dihydropyrimidin-5-yl))(1-{[3-fluorophenyl]methyl}-pyrazol-4-yl)carboxamide;

N-(6-amino-1-methyl-2,4-dioxo-3-cyclopropylmethyl(1,3-dihydropyrimidin-5-yl))(1-{[3-fluorophenyl]methyl}-pyrazol-4-yl)carboxamide;

N-(6-amino-1-ethyl-2,4-dioxo-3-cyclopropylmethyl (1,3-dihydropyrimidin-5-yl))(1-{[3-fluorophenyl]methyl}-pyrazol-4-yl)carboxamide;

N-[6-amino-3-(cyclopropylmethyl)-1-methyl-2,4-dioxo(1,3-dihydropyrimidin-5-yl)][1-benzylpyrazol-4-yl]carboxamide;

N-(6-amino-1-methyl-2,4-dioxo-3-cyclopropylmethyl(1,3-dihydropyrimidin-5-yl))(1-{[3-cyanophenyl]methyl}-pyrazol-4-yl)carboxamide;

[1-(2-(1H-1,2,3,4-tetraazol-5-yl)ethyl)pyrazol-4-yl]-N-[6-amino-3-(cyclopropylmethyl)-1-methyl-2,4-dioxo(1,3-dihydropyrimidin-5-yl)]carboxamide;

N-[6-amino-3-(cyclopropylmethyl)-1-ethyl-2,4-dioxo(1,3-dihydropyrimidin-5-yl)] (1-{[6-(trifluoromethyl)(3-pyridyl)]methyl}pyrazol-4-yl)carboxamide;

N-[6-amino-3-propyl)-1-ethyl-2,4-dioxo(1,3-dihydropyrimidin-5-yl)](1-{(2-pyridyl)]methyl}pyrazol-4-yl)carboxamide;

N-[6-amino-3-(2-methylpropyl)-1-methyl-2,4-dioxo(1,3-dihydropyrimidin-5-yl)][1-benzylpyrazol-4-yl]carboxamide;

N-[6-amino-3-(2-methylpropyl)-1-methyl-2,4-dioxo(1,3-dihydropyrimidin-5-yl)][1-{[3-fluorophenyl]methyl}pyrazol-4-yl]carboxamide;

N-[6-amino-3-(2-methylpropyl)-1-ethyl-2,4-dioxo(1,3-dihydropyrimidin-5-yl)][1-{[3-fluorophenyl]methyl}pyrazol-4-yl]carboxamide;

N-[6-amino-3-(2-methylpropyl)-1-methyl-2,4-dioxo(1,3-dihydropyrimidin-5-yl)][1-{[3-(trifluoromethyl)phenyl]methyl}pyrazol-4-yl]carboxamide; and N-[6-amino-3-(2-methylpropyl)-1-ethyl-2,4-dioxo(1,3-dihydropyrimidin-5-yl)](1-{[6-(trifluoromethyl)(3-pyridyl)]methyl}pyrazol-4-yl)carboxamide.

Example 14

Preparation of a Compound of Formula I

A. Preparation of a Compound of Formula I in which $R^1$ is n-Propyl, $R^2$ is Ethyl, X is 1,4-Pyrazolyl, Y is Methylene, and Z is 3-Trifluoromethylphenyl

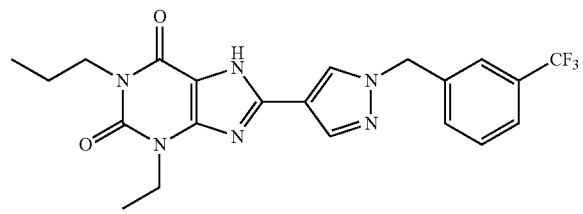

A mixture of N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide (850 mg, 2.34 mmol), 10% aqueous sodium hydroxide (10 ml), and methanol (10 ml) was stirred at 100° C. for 18 hours. The mixture was cooled, methanol removed under reduced pressure, and the remaining mixture was acidified with hydrochloric acid to pH 2. The precipitate was filtered off, washed with water/methanol mixture, to provide 3-ethyl-1-propyl-8-(1-{[3-(trifluoromethyl)phenyl]methyl}pyrazol-4-yl)-1,3,7-trihydropurine-2,6-dione, a compound of Formula I.

$^1$H-NMR (DMSO-d6) δ 8.57 (s, 1H), 8.15 (s, 1H), 7.60-7.75 (m, 4H), 5.54 (s, 2H), 4.05-4.50 (m, 2H), 3.87-3.91 (m, 2H), 1.55-1.64 (m, 2H), 1.25 (t, 3H, J=7.03 Hz), 0.90 (t, 3H, J—7.42 Hz); MS m/r 447.2 (M$^+$)

B. Preparation of a Compound of Formula I, Varying $R^1$, $R^2$, X, Y, and Z

Similarly, following the procedure of Example 14A, but replacing N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide with other compounds of formula (13), other compounds of Formula I are prepared, including those listed in Example 8.

Example 15

Preparation of a Compound of Formula (14)

A. Preparation of a Compound of Formula (14) in which $R^2$ is Ethyl

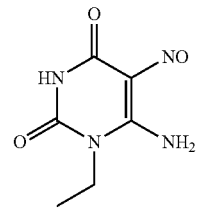

To a solution of 6-amino-1-ethyl-1,3-dihydropyrimidine-2,4-dione (5.0 g, 32.3 mmol) in a mixture of 50% acetic acid/water (50 ml) at 70° C. was added sodium nitrite (4.45 g, 64.5 mmol) in portions over a period of 30 minutes. The mixture was stirred at 70° C. for a further 30 minutes. The reaction mixture was cooled, and the precipitate filtered off, and washed with water, then methanol, to provide 6-amino-1-ethyl-5-nitroso-1,3-dihydropyrimidine-2,4-dione, a compound of formula (14).

$^1$H-NMR (DMSO-d6): δ 11.52 (s, 1H), 9.16 (s, 1H), 3.83 (q, 2H, J=7.0 Hz), 1.11 (t, 3H, J=7.0 Hz). MS m/z 184.8 (M$^+$), 206.80 (M$^+$+Na)

B. Preparation of a Compound of Formula (14), Varying $R^2$

Similarly, following the procedure of Example 15A, but replacing 6-amino-1-ethyl-1,3-dihydropyrimidine-2,4-dione with 6-amino-1-methyl-1,3-dihydropyrimidine-2,4-dione, 6-amino-1-methyl-5-nitroso-1,3-dihydropyrimidine-2,4-dione was prepared.

C. Preparation of a Compound of Formula (14), Varying $R^2$

Similarly, following the procedure of Example 15A, but replacing 6-amino-1-ethyl-1,3-dihydropyrimidine-2,4-dione with other compounds of formula (5), other compounds of formula (14) are prepared.

Example 16

Preparation of a Compound of Formula (15)

A. Preparation of a Compound of Formula (15) in which $R^2$ is Ethyl

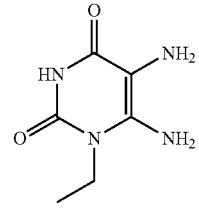

To a solution of 6-amino-1-ethyl-5-nitroso-1,3-dihydropyrimidine-2,4-dione (3.9 g, 21.2 mmol) in 14.5% aqueous ammonia (50 ml) at 50° C. was added sodium dithionite (Na$_2$S$_2$O$_4$, 7.37 g, 42.4 mmol) in portions over 15 minutes, and the mixture was stirred for 20 minutes. The solution was concentrated under reduced pressure to a volume of 30 ml, cooled to 5° C., the precipitate filtered off, and washed with cold water, to provide 5,6-diamino-1-ethyl-1,3-dihydropyrimidine-2,4-dione, a compound of formula (15).

$^1$H-NMR (DMSO-d6): δ 10.58 (s, 1H), 6.18 (s, 2H), 3.83 (q, 2H, J=7.2 Hz), 2.82 (s, 2H), 1.10 (t, 3H, J=7.2 Hz).

B. Preparation of a Compound of Formula (15), Varying $R^2$

Similarly, following the procedure of Example 16A, but replacing 6-amino-1-ethyl-5-nitroso-1,3-dihydropyrimidine-2,4-dione with 6-amino-1-methyl-5-nitroso-1,3-dihydropyrimidine-2,4-dione, 5,6-diamino-1-methyl-1,3-dihydropyrimidine-2,4-dione was prepared.

C. Preparation of a Compound of Formula (15), Varying $R^2$

Similarly, following the procedure of Example 16A, but replacing 6-amino-1-ethyl-5-nitroso-1,3-dihydropyrimidine-2,4-dione with other compounds of formula (14), other compounds of formula (15) are prepared.

Example 17

Preparation of a Compound of Formula (16)

A. Preparation of a Compound of Formula (16) in which $R^2$ is Ethyl, X is 1,4-Pyrazolyl, Y is Methylene, and Z is 3-Trifluoromethylphenyl

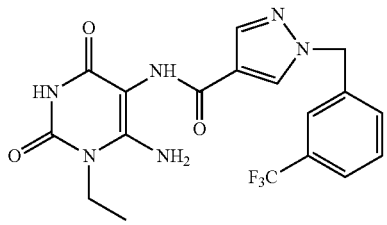

To a mixture of 5,6-diamino-1-ethyl-1,3-dihydropyrimidine-2,4-dione (2 g, 11.76 mmol) and 1-{[3-(trifluoromethyl)phenyl]methyl}pyrazole-4-carboxylic acid (3.5 g, 12.94 mmol) in methanol (50 ml) was added 1-(3-dimethylaminopropyl)-3-ethylcarbodiimide hydrochloride (2.47 g, 12.94 mmol), and the reaction mixture was stirred for 16 hours at room temperature. Solvent was removed under reduced pressure, and the residue was washed with water and methanol. The product was dried under vacuum to provide N-(6-amino-1-ethyl-2,4-dioxo(1,3-dihydropyrimidin-5-yl))(1-{[3-(trifluoromethyl)phenyl]methyl}pyrazol-4-yl)carboxamide, a compound of formula (16).

$^1$H-NMR (DMSO-d6): δ 10.60 (s, 1H), 8.50 (s, 1H), 8.39 (s, 1H), 8.01 (s, 1H), 7.72-7.50 (m, 4H), 6.69 (s, 2H), 5.50 (s, 2H), 3.87 (q, 2H, J=7.2 Hz), 1.11 (t, 3H, 7.2 Hz); MS m/z 421 (M⁻)

B. Preparation of a Compound of Formula (16), Varying $R^2$, X, Y, and Z

Similarly, following the procedure of Example 17A, but replacing 5,6-diamino-1-ethyl-1,3-dihydropyrimidine-2,4-dione with 5,6-diamino-1-methyl-1,3-dihydropyrimidine-2,4-dione, N-(6-amino-1-methyl-2,4-dioxo(1,3-dihydropyrimidin-5-yl))(1-{[3-(trifluoromethyl)phenyl]methyl}pyrazol-4-yl)carboxamide was prepared.

C. Preparation of a Compound of Formula (16), Varying $R^2$, X, Y, and Z

Similarly, following the procedure of Example 16A, but replacing 5,6-diamino-1-ethyl-1,3-dihydropyrimidine-2,4-dione with other compounds of formula (14), other compounds of formula (15) are prepared.

Example 18

Preparation of a Compound of Formula (3)

A. Preparation of a Compound of Formula (3) in which $R^1$ is n-Propyl, $R^2$ is Ethyl, X is 1,4-Pyrazolyl, Y is Methylene, and Z is 3-Trifluoromethylphenyl

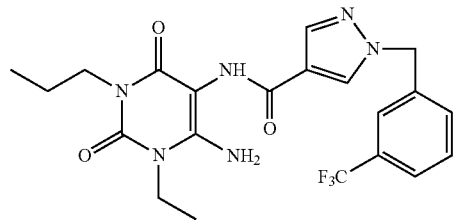

A mixture of a solution of N-(6-amino-1-ethyl-2,4-dioxo(1,3-dihydropyrimidin-5-yl))(1-{[3-(trifluoromethyl)phenyl]methyl}pyrazol-3-yl)carboxamide (1.5 g, 3.55 mmol) in dimethylformamide (30 ml), potassium carbonate (980 mg, 7.1 mmol) and propyl iodide (724 mg, 4.26 mmol) was stirred at room temperature overnight. Water was added, and the precipitate filtered off, to provide N-(6-amino-1-ethyl-2,4-dioxo-3-propyl(1,3-dihydropyrimidin-5-yl))(1-{[3-(trifluoromethyl)phenyl]methyl}pyrazol-4-yl)carboxamide, a compound of formula (3), which was used in the next reaction with no further purification.

$^1$H-NMR (DMSO-d6): δ 8.58 (s, 1H), 8.39 (s, 1H), 8.01 (s, 1H), 7.72-7.50 (m, 4H), 6.71 (s, 2H), 5.51 (s, 2H), 4.0-3.82 (m, 2H), 3.77-3.65 (m, 2H), 1.60-1.50 (m, 2H), 1.13 (t, 3H, J=6.8 Hz), 0.84 (t, 3H, J=7.2 Hz); MS m/z 462.9 (M⁻)

B. Preparation of a Compound of Formula (3), Varying $R^1$, $R^2$, X, Y, and Z

Similarly, following the procedure of Example 18A, but replacing N-(6-amino-1-ethyl-2,4-dioxo(1,3-dihydropyrimidin-5-yl))(1-{[3-(trifluoromethyl)phenyl]-methyl}pyrazol-3-yl)carboxamide with N-(6-amino-1-methyl-2,4-dioxo(1,3-dihydropyrimidin-5-yl)), N-(6-amino-1-methyl-2,4-dioxo-3-propyl(1,3-dihydropyrimidin-5-yl))(1-{[3-(trifluoromethyl)phenyl]methyl}pyrazol-4-yl)carboxamide was prepared.

C. Preparation of a Compound of Formula (3), Varying $R^1$, $R^2$, X, Y, and Z

Similarly, following the procedure of Example 18A, but optionally replacing N-(6-amino-1-ethyl-2,4-dioxo(1,3-dihydropyrimidin-5-yl))(1-{[3-(trifluoromethyl)phenyl]methyl}pyrazol-3-yl)carboxamide with other compounds of formula (15), and optionally replacing propyl iodide with other compounds of formula $R^1$Hal, other compounds of formula (3) are prepared.

Example 19

Preparation of a Compound of Formula I

A. Preparation of a Compound of Formula I in which $R^1$ is n-Propyl, $R^2$ is Ethyl, X is 1,4-Pyrazolyl, Y is Methylene, and Z is 3-Trifluoromethylphenyl

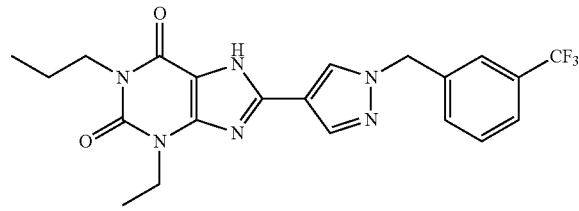

A mixture of N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide (300 mg, 464 mmol), 20% aqueous sodium hydroxide (5 ml), and methanol (10 ml) was stirred at 80° C. for 3 hours. The mixture was cooled, methanol removed under reduced pressure, and the remaining mixture was acidified with hydrochloric acid to pH 2. The precipitate was filtered off, washed with water and methanol, to provide 3-ethyl-1-propyl-8-(1-{[3-(trifluoromethyl)phenyl]methyl}pyrazol-4-yl)-1,3,7-trihydropurine-2,6-dione, a compound of Formula I.

$^1$H-NMR (DMSO-d6) δ 8.57 (s, 1H), 8.15 (s, 1H), 7.60-7.75 (m, 4H), 5.54 (s, 2H), 4.05-4.50 (m, 2H), 3.87-3.91 (m, 2H), 1.55-1.64 (m, 2H), 1.25 (t, 3H, J=7.03 Hz), 0.90 (t, 3H, J=7.42 Hz); MS m/z 447.2 (M$^+$)

Example 20

Characterization of $A_{2B}$ Antagonists

Radioligand Binding for $A_{2B}$ Adenosine Receptor

Human $A_{2B}$ adenosine receptor cDNA was stably transfected into HEK-293 cells (referred to as HEK-A2B cells). Monolayers of HEK-A2B cells were washed with PBS once and harvested in a buffer containing 10 mM HEPES (pH 7.4), 10 mM EDTA and protease inhibitors. These cells were homogenized in polytron for 1 minute at setting 4 and centrifuged at 29000 g for 15 minutes at 4° C. The cell pellets were washed once with a buffer containing 10 mM HEPES (pH7.4), 1 mM EDTA and protease inhibitors, and were resuspended in the same buffer supplemented with 10% sucrose. Frozen aliquots were kept at −80° C.

Competition assays were started by mixing 10 nM $^3$H-ZM241385 (Tocris Cookson) with various concentrations of test compounds and 50 μg membrane proteins in TE buffer (50 mM Tris and 1 mM EDTA) supplemented with 1 Unit/mL adenosine deaminase. The assays were incubated for 90 minutes, stopped by filtration using Packard Harvester and washed four times with ice-cold TM buffer (10 mM Tris, 1 mM MgCl2, pH 7.4). Non specific binding was determined in the presence of 10 μM ZM241385. The affinities of compounds (i.e. Ki values) were calculated using GraphPad software.

Radioligand Binding for Other Adenosine Receptors

Human $A_1$, $A_{2A}$, $A_3$ adenosine receptor cDNAs were stably transfected into either CHO or HEK-293 cells (referred to as CHO-$A_1$, HEK-$A_{2A}$, CHO-$A_3$). Membranes were prepared from these cells using the same protocol as described above. Competition assays were started by mixing 0.5 nM $^3$H—CPX (for CHO-$A_1$), 2 nM $^3$H-ZM214385 (HEK-$A_{2A}$) or 0.1 nM $^{125}$I-AB-MECA (CHO-$A_3$) with various concentrations of test compounds and the perspective membranes in TE buffer (50 mM Tris and 1 mM EDTA of CHO-$A_1$ and HEK-$A_{2A}$) or TEM buffer (50 mM Tris, 1 mM EDTA and 10 mM MgCl$_2$ for CHO-$A_3$) supplemented with 1 Unit/mL adenosine deaminase. The assays were incubated for 90 minutes, stopped by filtration using Packard Harvester and washed four times with ice-cold TM buffer (10 mM Tris, 1 mM MgCl$_2$, pH 7.4). Non specific binding was determined in the presence of 1 μM CPX (CHO-$A_1$), 1 μM ZM241385 (HEK-$A_{2A}$) and 1 μM IB-MECA (CHO-$A_3$). The affinities of compounds (i.e. Ki values) were calculated using GraphPad™ software.

cAMP Measurements

Monolayer of transfected cells were collected in PBS containing 5 mM EDTA. Cells were washed once with DMEM and resuspended in DMEM containing 1 Unit/mL adenosine deaminase at a density of 100,000-500,000 cells/ml. 100 μl of the cell suspension was mixed with 25 μl containing various agonists and/or antagonists and the reaction was kept at 37° C. for 15 minutes. At the end of 15 minutes, 125 μl 0.2N HCl was added to stop the reaction. Cells were centrifuged for 10 minutes at 1000 rpm. 100 μl of the supernatant was removed and acetylated. The concentrations of cAMP in the supernatants were measured using the direct cAMP assay from Assay Design. $A_{2A}$ and $A_{2B}$ adenosine receptors are coupled to Gs proteins and thus agonists for $A_{2A}$ adenosine receptor (such as CGS21680) or for $A_{2B}$ adenosine receptor (such as NECA) increase the cAMP accumulations whereas the antagonists to these receptors prevent the increase in cAMP accumulations-induced by the agonists. $A_1$ and $A_3$ adenosine receptors are coupled to Gi proteins and thus agonists for $A_1$ adenosine receptor (such as CPA) or for $A_3$ adenosine receptor (such as IB-MECA) inhibit the increase in cAMP accumulations-induced by forskolin. Antagonists to $A_1$ and $A_3$ receptors prevent the inhibition in cAMP accumulations.

Real-time RT-PCR was performed to determine the expression levels of the adenosine receptor (AdoR) subtypes on primary cultured human hepatic stellate cells (HHSCs). Among the four subtypes of AdoRs, the $A_{2B}$ AdoR was expressed at the highest level. In addition, using cellular cAMP concentration as a functional readout, our results indicated that $A_{2B}$ AdoRs are functionally expressed on HHSCs, whereas $A_1$, $A_{2A}$, or $A_3$ AdoRs are not. The effect of adenosine or NECA, a stable analog of adenosine, on the expression of the inflammatory cytokines was determined using ELISA. Adenosine and NECA increased the release of IL-6 in a concentration-dependent manner with a maximal increase of 11.9±3.1 fold over the basal level. In addition, NECA increased the expression of α-smooth muscle actin and α-1 pro-collagen and the production of collagen from HHSCs. The effects of NECA were completely abolished by the $A_{2B}$ AdoR antagonist and partially blocked by an IL-6 neutralizing antibody.

Example 21

Effect of $A_{2B}$ Antagonist on Human Hepatic Stellate Cells

Abbreviations
 Ab Antibody
 AdoR Adenosine receptor
 ADA adenosine deaminase
 ANOVA analysis of variance
 AST aspartate aminotransferae
 CPA N6-cyclopentyladenosine DMEM Dulbecco's modified Eagle's medium
DMSO dimethyl sulfoxide
DNase deoxyribonuclease
HEPES 4-(2-hydroxyethyl)-1-piperazineethanesulfonic acid
HHSCs human hepatic stellate cells
NECA 5'-(N-ethylcarboxamido)-adenosine Materials and Methods Materials Selective antagonists to the $A_{2B}$ receptor (8-(1-{[5-(4-chlorophenyl)(1,2,4-oxadiazol-3-yl)]methyl}pyrazol-4-yl)-1-propyl-1,3,7-trihydropurine-2,6-dione (compound (1)) and 3-ethyl-1-propyl-8-(1-{[3-(trifluoromethyl)phenyl]methyl}pyrazol-4-yl)-1,3,7-trihydropurine-2,6-dione (compound (2)) were synthesized by the Department of Bio-Organic Chemistry at CV Therapeutics Inc. (Palo Alto, Calif.), and was described in our earlier publication Zhong et al. (2004) Am J Respir Cell Mol Biol; 30(1):118-125. All other reagents, such as rolipram, forskolin, NECA, and adenosine deaminase (ADA), etc., were purchased from Sigma (St. Louis, Mo.) unless otherwise stated.

Cell Culture

Primary cultured normal human hepatic stellate Cells (HHSCs) were obtained from ScienCell Research Laboratories (San Diego, Calif.) and cultured using stellate cell growth medium (ScienCell Research Laboratories). HHSCs were routinely grown in a humidified incubator with 5% $CO_2$ at 37° C. and reseeded when they reached about 80-90% confluency. Each re-seeding is called a passage. Cells from passages 2 to 5 were used in the following studies.

Stimulation of HHSCs

HHSCs were seeded into 12-well tissue culture plates at a density of $1 \times 10^5$ cells/well in stellate cell growth medium and allowed to adhere overnight and reach ~90% confluency. Cells were washed twice in HEPES buffered saline, and cultured in DMEM containing various agonists or antagonists of AdoRs for 1 or 24 h.

RNA Extraction and Real-Time RT-PCR

Total RNA was extracted from HHSCs using the Stratagene Absolutely RNA™ RT-PCR Miniprep Kit followed by DNase treatment to eliminate potential genomic DNA contamination. Real-time RT-RCR for adenosine receptors was performed as previously described in Zhong et al. (2004) Am J Respir Cell Mol Biol; 30(1):118-125.

The specific primers for α-smooth muscle actin used were:

```
forward:
5' TGGGAATGGGACAAAAAGACA3';      (SEQ ID NO.: 1)
and reverse:
5' CGGGTACTTCAGGGTCAGGAT3',      (SEQ ID NO.: 2)
``` while the primers for α-1 pro-collagen were:

```
forward:
5' CACCAATCACCTGCGTACAGA3';      (SEQ ID NO.: 3)
and reverse:
5' CAGATCACGTCATCGCACAAC3',      (SEQ ID NO.: 4)
``` and each of these primers were designed using Primer Express 2.0 (Applied Biosystems) following the recommended guidelines based on sequences from Genbank. At the end of the PCR cycle, a dissociation curve was generated to ensure the amplification of a single product, and the threshold cycle time (Ct value) for each gene was determined. Relative mRNA levels were calculated based on the Ct values, normalized to β-actin in the same sample, and presented as percentages of β-actin mRNA.

Measurement of cAMP Accumulation

Cells were harvested using 0.0025% trypsin and 2 mM EDTA in PBS, washed and resuspended in phenol-free DMEM to a concentration of $1 \times 10^6$ cells/ml, and then incubated with 1 U/ml of ADA for 30 min at room temperature. Cells were then treated with AdoR agonists, antagonists, and forskolin in the presence of 50 µM of the phosphodiesterase IV inhibitor, rolipram. After incubating for 15 min at 37° C., cells were lysed and cAMP concentrations were determined using cAMP-Screen Direct™ System (Applied Biosystems) according to the manufacturer's instructions.

Measurement of IL-6, Collagen and Aspartate Aminotransferae (AST)

The concentration of IL-6 in the cell medium was determined using ELISA kits obtained from Biosource (Camarillo, Calif.) according to the manufacturer's instructions. The minimal detection levels of IL-6 with these kits were 2 pg/ml. The concentration of soluble collagen in the cell medium was measured using the Sircol collagen assay (Biocolor Ltd., Belfast N. Ireland) according to manufacture's instructions. The activity of AST in mouse plasma was determined using the Infinity™ AST assay (Thermo Electron Corporation, Waltham, Mass.)

Mice

Adenosine deaminase (ADA)-deficient mice were generated and genotyped as described in Blackburn et al. (1998), J Biol Chem, 273(9):5093-5100. Mice homozygous for the null Ada allele were designated ADA-deficient ($ADA^{-/-}$), while mice heterozygous for the null Ada allele were designated as ADA control mice ($ADA^+$). All mice were on a mixed 129sv/C57BL/6J background and all phenotypic comparisons were performed amongst littermates. Animal care was in accordance with institutional and NIH guidelines. Mice were housed in ventilated cages equipped with microisolator lids and maintained under strict containment protocols. No evidence of bacterial, parasitic, or fungal infection was found, and serologies on cage littermates were negative for 12 of the most common murine viruses.

Antagonist Treatment $ADA^{-/-}$ mice were identified at birth by screening for ADA enzymatic activity in the blood as described by Young et al. (2004) J Immunol, 173(2):1380-1389. $ADA^{-/-}$ mice were maintained on ADA enzyme therapy from postnatal day 2 until postnatal day 21 also as described in Young et al. (2004). At this stage, treatments with compound (2) (1 mg/kg per injection) or vehicle (corn oil/ethanol/DMSO) were initiated. Treatments consisted of an intra-peritoneal i.p. injection in the morning and in the evening for 17 days. Treatment groups included $ADA^{-/-}$ or $ADA^+$ mice receiving compound (2), vehicle or no treatment. All mice were littermates and both males and females were included in these experiments.

Statistical Analysis

Data were presented as mean±SEM of at least three separate experiments. The statistical analysis was performed using a two-tailed Student's t-test, or ANOVA followed by Newman-Keuls test for multiple comparisons. A p value of <0.05 was considered significant.

Results

Expression of AdoR Subtypes in HHSCs

Real-time RT-PCR was performed to quantify the levels of transcripts for AdoRs. Among the four subtypes, the $A_{2B}$ receptor had the highest transcript level (FIG. 1). Lower levels of $A_1$ and $A_{2A}$ receptor transcripts were also detected, whereas the transcript for $A_3$ receptors was below the detection level. Hence, the rank order of AdoR mRNA levels was $A_{2B} \gg A_{2A} > A_1 \gg A_3$.

Figure 2:
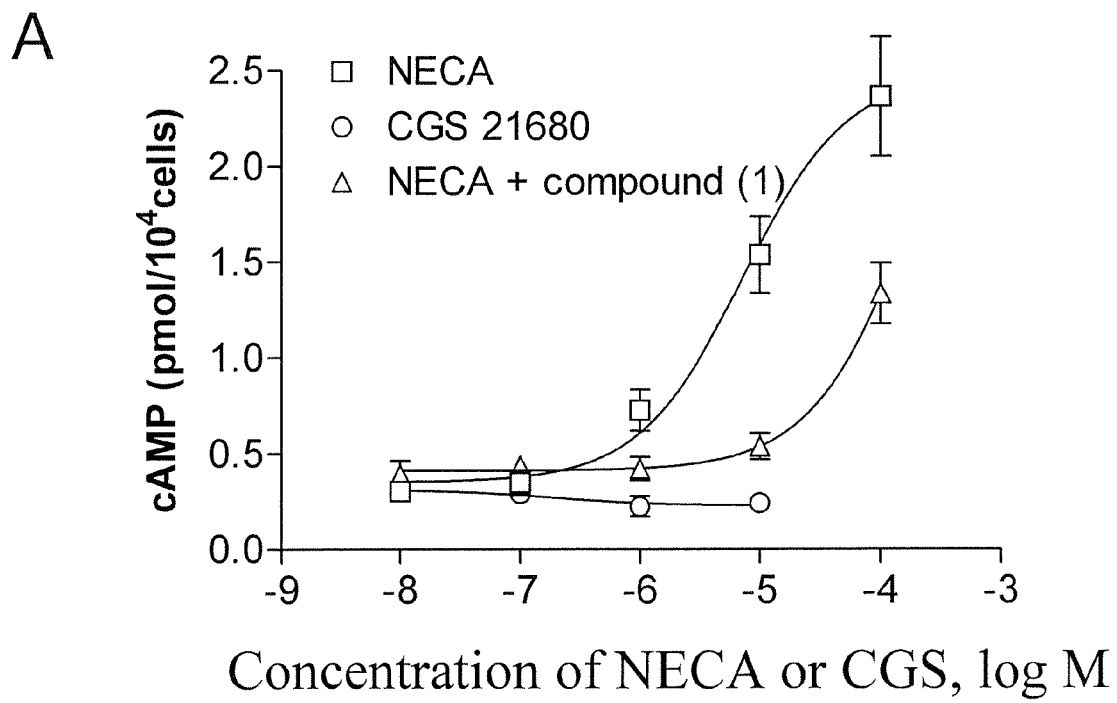
FIG. 2 shows the effects of AdoR agonists and antagonist on cellular cAMP accumulation in HHSCs. (A) Concentration-response curves of CGS-21680 (CGS, circle) and NECA in the absence (square) or presence (triangle) of the $A_{2B}$ receptor antagonist 8-(1-{[5-(4-chlorophenyl)(1,2,4-oxadiazol-3-yl)]methyl}pyrazol-4-yl)-1-propyl-1,3,7-trihydropurine-2,6-dione (compound (1)) (1 µM). (B) Lack of effect of CPA (1 µM) and IB-MECA (1M, 1 µM) on forskolin (Fsk, 10 µM)-induced cellular cAMP accumulation. Data shown are averages±SEM (n=6 in A and n=5 in B).
Figure 2:
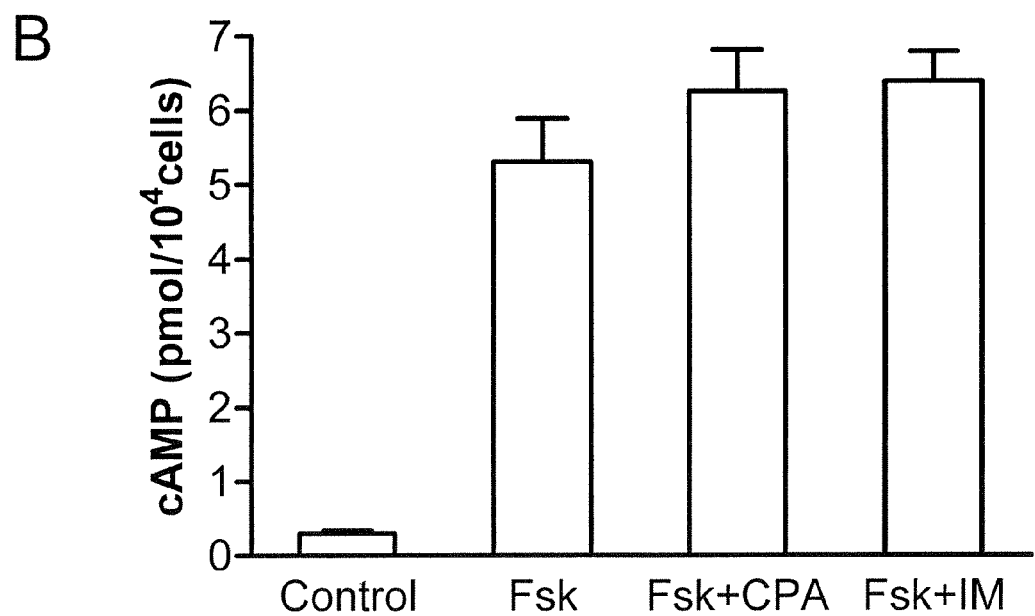

In many cell types, activation of $A_{2A}$ or $A_{2B}$ receptors leads to increases in cellular cAMP accumulation, whereas activation of $A_1$ or $A_3$ receptors decreases cellular cAMP accumulation caused by the adenylate cyclase activator, forskolin. To identify the AdoR subtype(s) that are functionally expressed in HHSCs, the effects of a non-selective agonist NECA and several other selective agonists on cellular cAMP accumulation were determined. NECA is a stable analog of adenosine, and it activates all four AdoR subtypes including $A_{2B}$ receptors. As shown in FIG. 2A, NECA increased cellular cAMP accumulation in a concentration-dependent manner. In contrast, the $A_{2A}$ selective agonist CGS-21680 (=10 μM) did not cause a significant increase in cellular cAMP concentration. In addition, the $A_1$ selective agonist, CPA (1 μM), and the $A_3$ selective agonist, IB-MECA (1 μM), failed to inhibit the cellular cAMP accumulation caused by forskolin (10 μM, FIG. 2B).

Because there is no selective agonist for $A_{2B}$ receptors, the effect of a selective antagonist to $A_{2B}$ receptors, compound (1), on NECA-induced cellular cAMP accumulation was determined. Compound (1) has a high affinity for the $A_{2B}$ receptor Ki=7 nM) and very low affinity for three other AdoR subtypes (Ki values are more than 5 μM for $A_1$, $A_{2A}$, and $A_3$ receptors) (Zhong et al. (2004) and Zhong et al. (2005) *Am J Respir Cell Mol Biol*, 32(1):2-8). As shown in FIG. 2A, compound (1) (1 μM) significantly attenuated NECA-induced cellular cAMP accumulation. Thus, using cellular cAMP concentration as readout for the functional expression of AdoRs, the results indicate that $A_{2B}$ receptors are functionally expressed in HHSCs whereas $A_1$, $A_{2A}$, or $A_3$ receptors are not.

Figure 3:
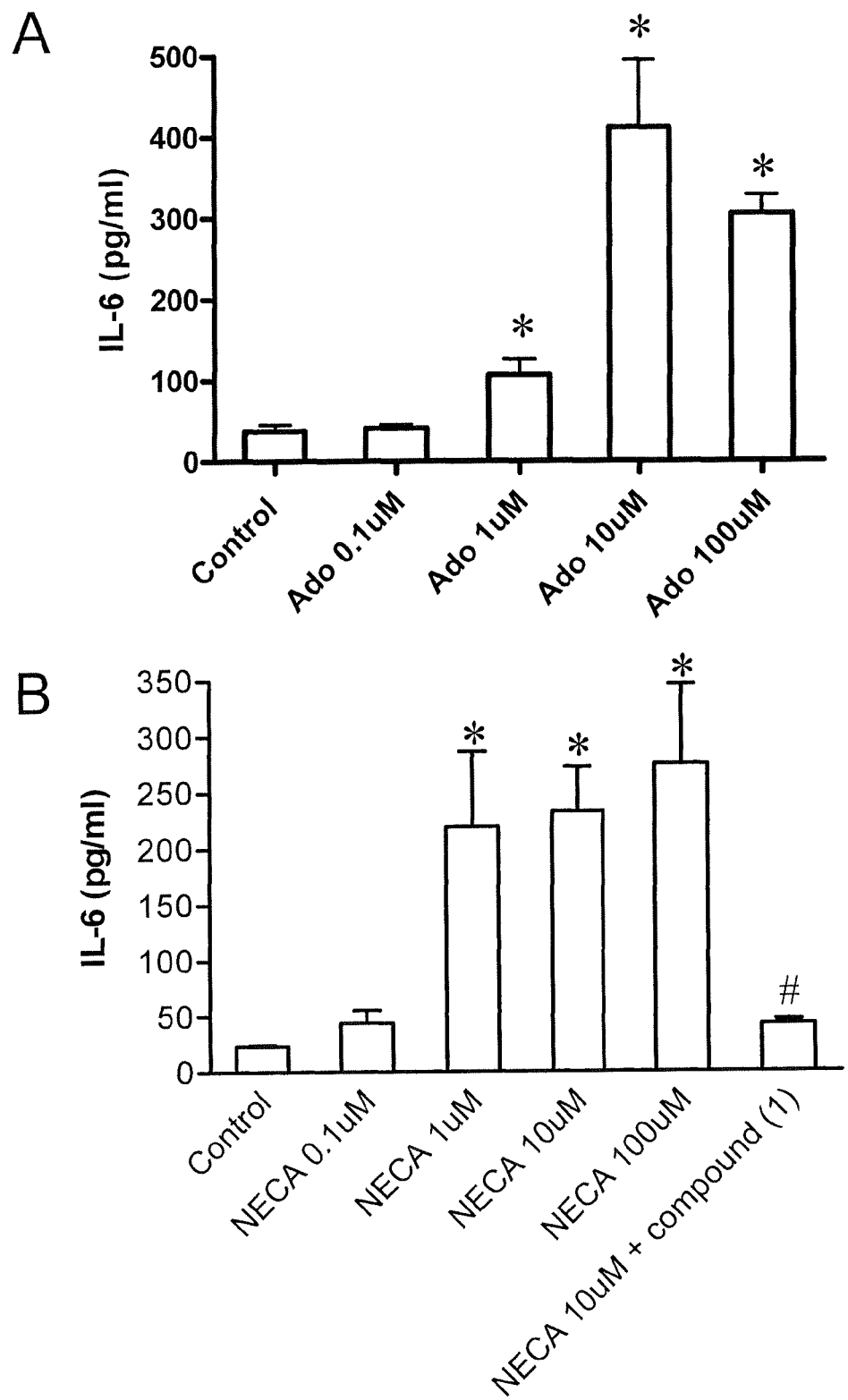
FIG. 3 graphs the effects of adenosine (A) and NECA (B) on the release of IL-6 by HHSCs. Cells were treated with vehicle, adenosine and NECA in the absence or presence of compound (1) for 24 h. Media from treated cells were collected, and the concentrations of IL-6 were determined using ELISA. Data shown are the averages±SEM (n=3). *: $p<0.05$, compared to control; #: $p<0.05$, compared to NECA (10 µM)-treated cells in B.

Activation of the $A_{2B}$ Receptor Increased the Release of IL-6 from HHSCs The concentrations of IL-6 in the culture media from cells treated with adenosine and NECA were measured using ELISA. As shown in FIG. 3, both adenosine and NECA increased IL-6 release in a concentration-dependent manner. NECA (100 μM) caused 11.9±3.1 fold increase of IL-6 release compared to vehicle-treated cells. To determine the role of $A_{2B}$ receptors in NECA-induced IL-6 production, cells were incubated with compound (1) (1 μM) together with NECA (10 μM). The $A_{2B}$ receptor antagonist, compound (1) (1 μM) reduced the NECA-increased IL-6 release by 90.7±0.1% (FIG. 3B). These results confirmed that NECA-induced IL-6 release is mediated by the $A_{2B}$ receptor subtype.

Effect of NECA on Expression of α-Smooth Muscle Actin and α-1 Pro-Collagen

Figure 4:
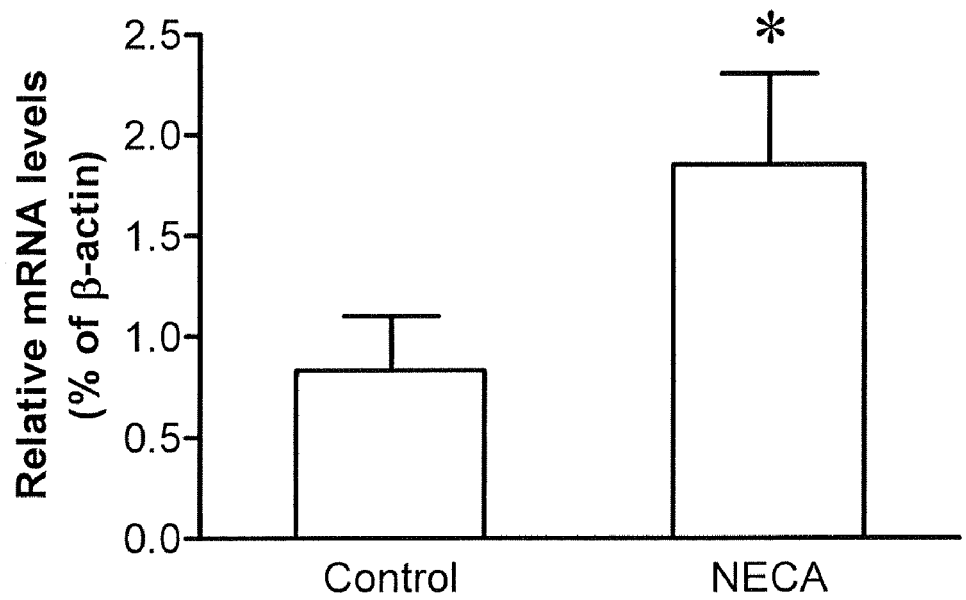
FIG. 4 shows the effects of NECA on the mRNA levels of α-smooth muscle actin (A) and α-1 pro-collagen (B) determined using real-time RT-PCR. HHSCs were incubated with NECA (10 µM) for 1 h. Cells incubated with vehicle were used as control. The expression levels of the target mRNA were normalized to that of β-actin. Data shown are averages±SEM (n=4 in A, and n=5 in B). *: $p<0.05$, compared to control.
Figure 4:
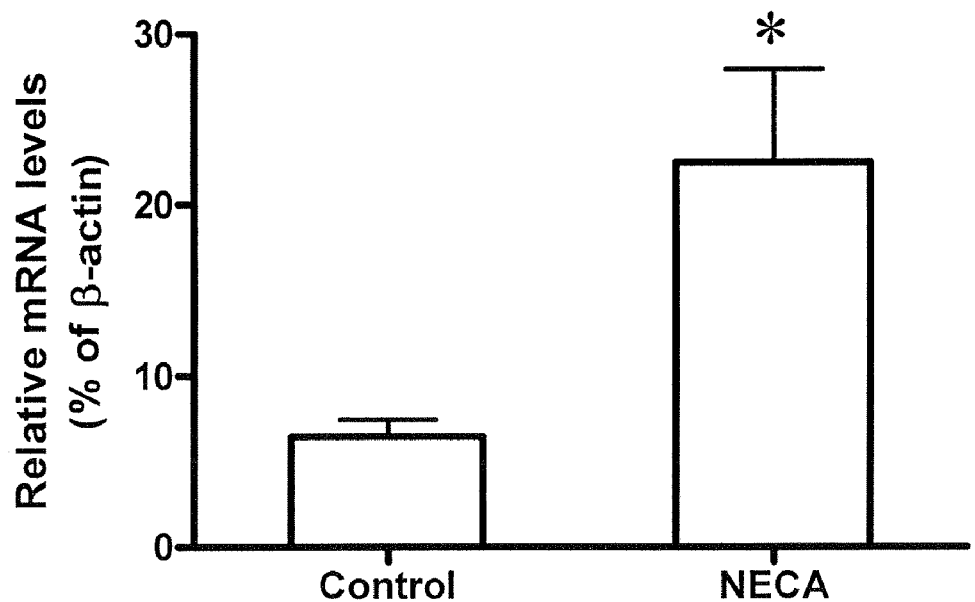

Activation of HHSC with accumulation of interstitial collagens is a hallmark of liver fibrosis. α-smooth muscle actin is a marker for myofibroblast and hence increased expression of α-smooth muscle actin is an indicator for HHSC differentiation into myofibroblast. The effect of NECA on expression of α-smooth muscle actin and α-1 pro-collagen was determined using real-time RT-PCR. As shown in FIG. 4, NECA significantly increased the expression of both α-smooth muscle actin (FIG. 4A) and α-1 pro-collagen (FIG. 4B). These results suggested that NECA may promote HHSC activation and collagen production.

Increased Collagen Production by Activation of the $A_{2B}$ Receptor is Partially Mediated by IL-6

Figure 5:
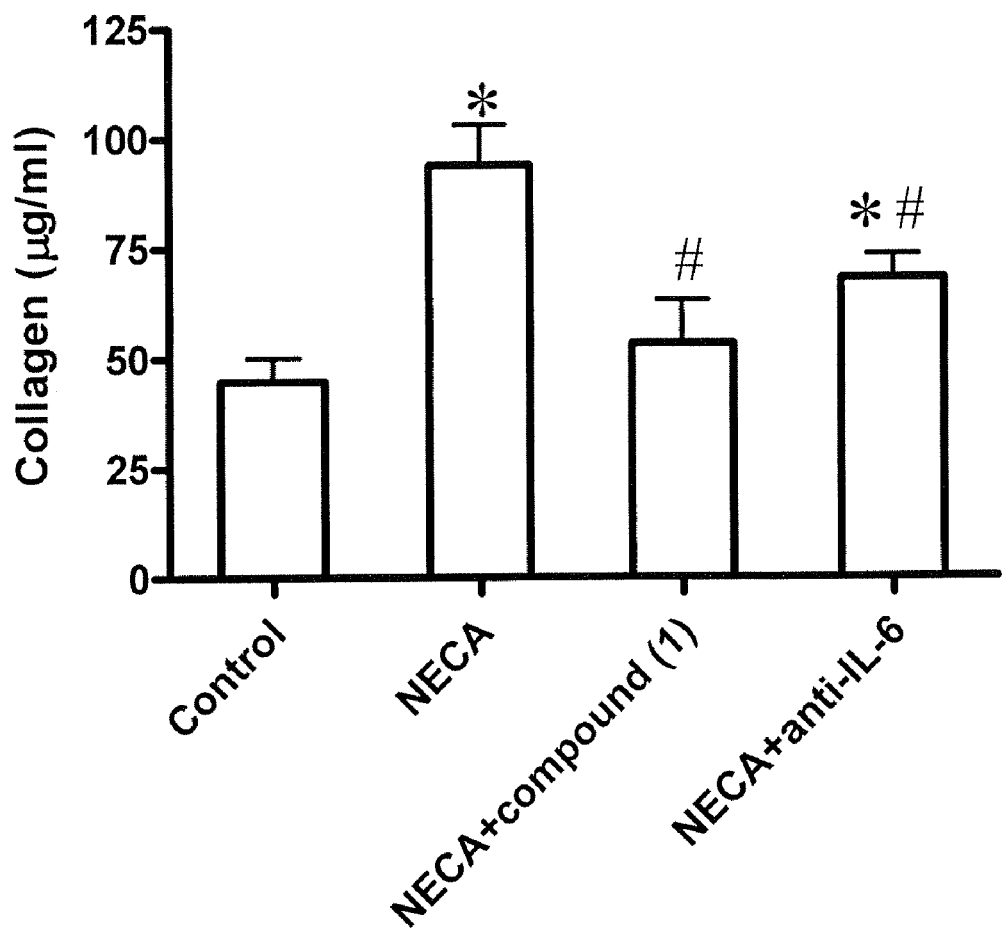
FIG. 5 illustrates the effects of NECA on collagen production by HHSCs. Cells were treated with vehicle, NECA in the absence or presence of compound (1) or anti-IL-6 antibody for 24 h. Media from treated cells were collected, and the concentrations of collagen were determined using Sircol collagen assay. Data shown are the averages±SEM (n=4-6). *: $p<0.05$, compared to control; #: $p<0.05$, compared to NECA (10 µM)-treated cells.

To confirm the role of NECA in collagen production, the concentrations of soluble collagen in the culture media from cells treated with NECA were measured. NECA caused a significant increase in release of collagen (FIG. 5). This effect of NECA was abolished by $A_{2B}$ antagonist, compound (1). To determine whether the effect of NECA on collagen production is dependent on the release of IL-6, the IL-6 neutralizing Ab was added to the cell media during NECA treatment. The IL-6 neutralizing Ab partially and significantly decreased the effect of NECA. These results demonstrate that activation of the $A_{2B}$ receptor leads to increased collagen production and this effect is partially mediated by released IL-6 from HHSCs.

Effect of $A_{2B}$ Receptor Antagonism on AST Levels in ADA-Deficient Mice

Figure 6:
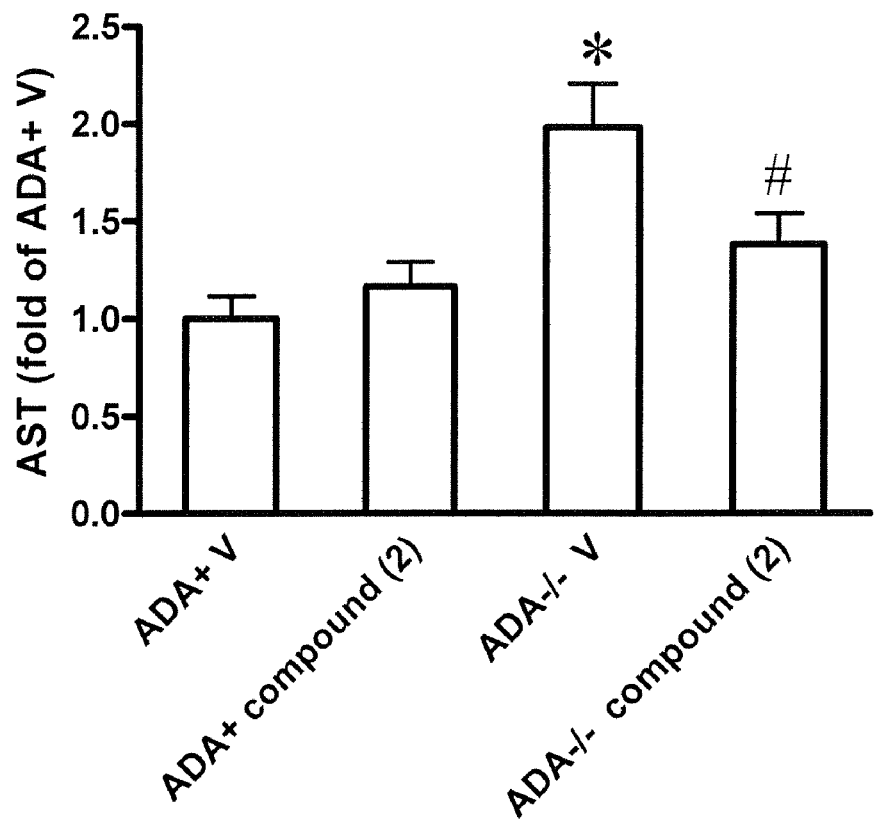
FIG. 6 illustrates the effects of $A_{2B}$ receptor antagonism on plasma AST levels in $ADA^{-/-}$ mice. Mouse plasma was collected in EDTA, and the activity of AST was determined using Infinity™ AST assay. Data shown are the averages±SEM (n=6-8). *: $p<0.05$, compared to $ADA^+$ treated with vehicle (ADA+V); #: $p<0.05$, compared to $ADA^{-/-}$ mice treated with vehicle (ADA-/- V).

ADA metabolizes adenosine; hence elevated adenosine levels are widespread among the tissues, including the liver of ADA-deficient mice, see Blackburn et al. (1998), *J Biol Chem*, 273(9):5093-5100. The plasma AST levels were examined in $ADA^+$ and $ADA^{-/-}$ mice treated with vehicle or compound (2). AST levels were elevated in $ADA^{-/-}$ mice compared to $ADA^+$ mice. Treatment of $ADA^{-/-}$ mice with compound (2) resulted in a significant reduction in AST levels (FIG. 6). These results suggest that $A_{2B}$ receptor antagonism can prevent AST elevation in $ADA^{-/-}$ mice.

We claim:

1. A method of decreasing the hepatotoxic side effects of chemotherapy or radiation by administering to a mammal undergoing such treatment a therapeutically effective amount of a compound having the name 3-ethyl-1-propyl-8-(1-{[3-(trifluoromethyl)phenyl]methyl}pyrazol-4-yl)-1,3,7-trihydropurine-2,6-dione and the chemical formula

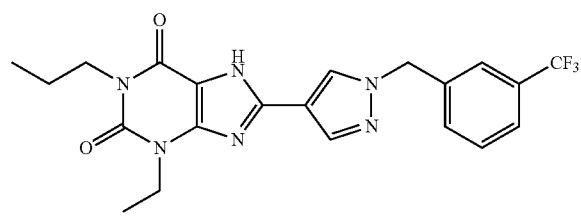

or a pharmaceutically acceptable salt thereof.

2. The method of claim 1, wherein the compound is administered prior to the initiation of chemotherapeutic or radiation treatment.

3. The method of claim 1, wherein compound is administered concurrently with the administration of the chemotherapeutic agent.

4. The method of claim 1, wherein the compound is administered orally.

5. The method of claim 1, wherein the compound is administered by IV.

6. The method of claim 1, wherein the mammal is human.

* * * * *